(12) United States Patent
Sultan et al.

(10) Patent No.: US 11,478,248 B2
(45) Date of Patent: Oct. 25, 2022

(54) PERCUTANEOUS VASCULAR SURGICAL SYSTEM AND METHOD

(71) Applicant: National University of Ireland Galway, Galway (IE)

(72) Inventors: Sherif Sultan, Galway (IE); Niamh Hynes, Galway (IE); Robert Miculas, Dublin (IE); Stefan Lohfeld, Lawrence, KS (US); Colin Henehan, Galway (IE)

(73) Assignee: National University of Ireland, Galway, Galway (IE)

( * ) Notice: Subject to any disclaimer, the term of this patent is extended or adjusted under 35 U.S.C. 154(b) by 93 days.

(21) Appl. No.: 16/612,643

(22) PCT Filed: May 10, 2018

(86) PCT No.: PCT/EP2018/062177
§ 371 (c)(1),
(2) Date: Jan. 21, 2020

(87) PCT Pub. No.: WO2018/206747
PCT Pub. Date: Nov. 15, 2018

(65) Prior Publication Data
US 2020/0197013 A1    Jun. 25, 2020

(30) Foreign Application Priority Data

May 12, 2017  (EP) .................................... 17170868

(51) Int. Cl.
*A61B 17/12*      (2006.01)
*A61B 90/00*      (2016.01)
(Continued)

(52) U.S. Cl.
CPC .... *A61B 17/1204* (2013.01); *A61B 17/12109* (2013.01); *A61B 17/12136* (2013.01);
(Continued)

(58) Field of Classification Search
CPC ....... A61M 25/1006; A61B 2090/3966; A61B 2017/22079; A61B 2017/22067;
(Continued)

(56) References Cited

U.S. PATENT DOCUMENTS 3,833,003 A * 9/1974 Taricco ............ A61B 17/12045
                                                604/509
4,672,974 A * 6/1987 Lee .................... A61B 5/02156
                                                600/486
(Continued)

FOREIGN PATENT DOCUMENTS

WO    2014184636 A2    11/2014

OTHER PUBLICATIONS

International Search Report and Written Opinion in corresponding International Application No. PCT/EP2018/062177.

*Primary Examiner* — Jocelin C Tanner
(74) *Attorney, Agent, or Firm* — Vitale, Vickrey, Niro & Gasey LLP

(57) ABSTRACT

The present invention provides a percutaneous vascular surgical system for performing endovascular/neurovascular interventions, the system incorporating a sheath having a proximal end and a distal end and defining a main lumen extending between the proximal and distal ends, an auxiliary lumen also defined by the sheath, a reversibly inflatable balloon located about the sheath adjacent the distal end and in fluid communication with the auxiliary lumen, a syringe selectively connectable to the main lumen to create suction through the main lumen, and a vessel closure device for the closure of the arteriotomy, the surgical system and method of the invention having utility in a large number of percutaneous vascular procedures such as carotid artery stenosis or neurovascular interventions and enabling four procedures to be performed with one system, being percutaneous (Continued)

access, emboli removal, flow reversal and arteriotomy closure.

26 Claims, 20 Drawing Sheets

(51) Int. Cl.
 *A61B 17/00* (2006.01)
 *A61B 17/22* (2006.01)
(52) U.S. Cl.
 CPC ............... *A61B 2017/00575* (2013.01); *A61B 2017/00778* (2013.01); *A61B 2017/22001* (2013.01); *A61B 2017/22054* (2013.01); *A61B 2017/22067* (2013.01); *A61B 2017/22079* (2013.01); *A61B 2090/3966* (2016.02)
(58) Field of Classification Search
 CPC ........... A61B 2017/22054; A61B 2017/22001; A61B 2017/0078; A61B 2017/00672; A61B 2017/00654; A61B 2017/0065; A61B 2017/00575; A61B 2017/00561; A61B 17/3421; A61B 17/22; A61B 17/12136; A61B 17/12109; A61B 17/1204; A61B 17/0057
 See application file for complete search history.

(56) References Cited

U.S. PATENT DOCUMENTS

| | | | | |
|---|---|---|---|---|
| 5,425,708 A * | 6/1995 | Nasu | ..................... | A61M 29/02 604/102.03 |
| 5,486,195 A | 1/1996 | Myers | | |
| 5,728,134 A * | 3/1998 | Barak | ................ | A61B 17/0057 128/899 |
| 5,851,210 A * | 12/1998 | Torossian | ................ | A61F 2/958 606/108 |
| 6,048,358 A * | 4/2000 | Barak | ................ | A61B 17/0057 606/213 |
| 6,315,768 B1 * | 11/2001 | Wallace | ............... | A61M 25/007 604/507 |
| 2004/0143290 A1 * | 7/2004 | Brightbill | ........ | A61B 17/00491 606/213 |
| 2007/0156084 A1 * | 7/2007 | Belhe | ............... | A61B 17/00491 604/57 |
| 2010/0204712 A1 * | 8/2010 | Mallaby | ........... | A61B 17/32037 606/128 |
| 2011/0144572 A1 * | 6/2011 | Kassab | ............. | A61M 25/0133 604/35 |
| 2011/0282383 A1 * | 11/2011 | Vidlund | .................. | A61M 5/19 606/213 |
| 2012/0265243 A1 * | 10/2012 | Phillips | ............... | A61B 17/0057 606/213 |
| 2012/0310269 A1 * | 12/2012 | Fearnot | ................. | A61L 31/146 606/191 |
| 2013/0190813 A1 * | 7/2013 | Tegels | ................ | A61B 17/0057 606/214 |
| 2013/0304118 A1 * | 11/2013 | Rakvica | ............. | A61B 17/0057 606/213 |
| 2014/0058440 A1 * | 2/2014 | Tegels | .................... | A61B 17/08 606/213 |
| 2014/0135831 A1 * | 5/2014 | White | ................ | A61B 17/0057 606/214 |
| 2014/0236224 A1 | 8/2014 | Tegels | | |
| 2015/0327843 A1 * | 11/2015 | Garrison | ............ | A61B 17/0057 606/213 |
| 2016/0106403 A1 | 4/2016 | Porter | | |
| 2018/0132837 A1 * | 5/2018 | Mathena | ................ | A61M 29/00 |

* cited by examiner

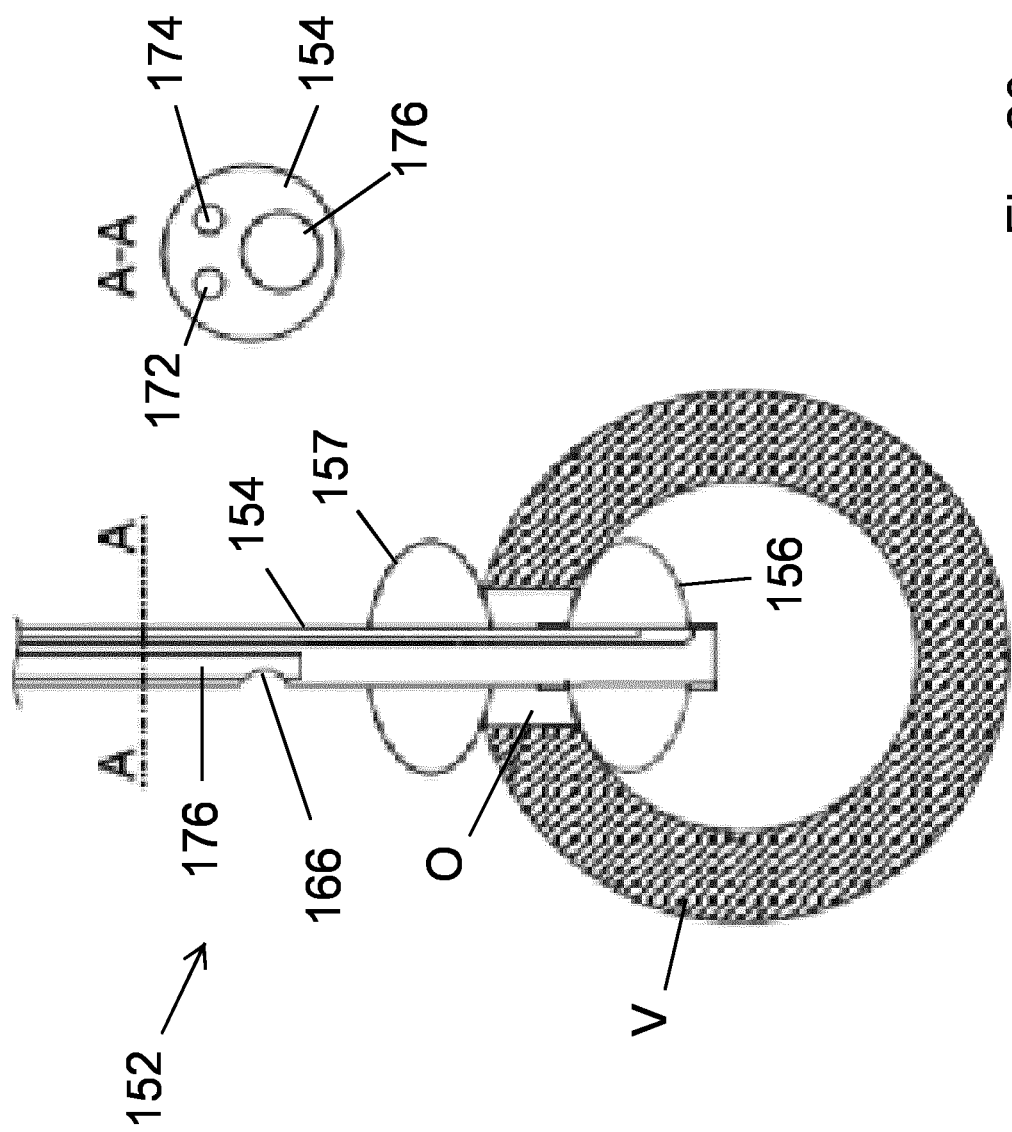

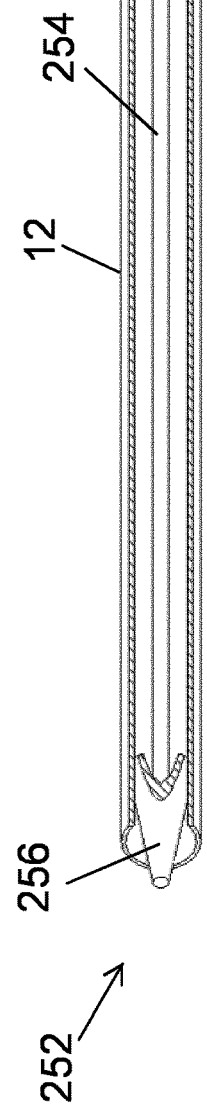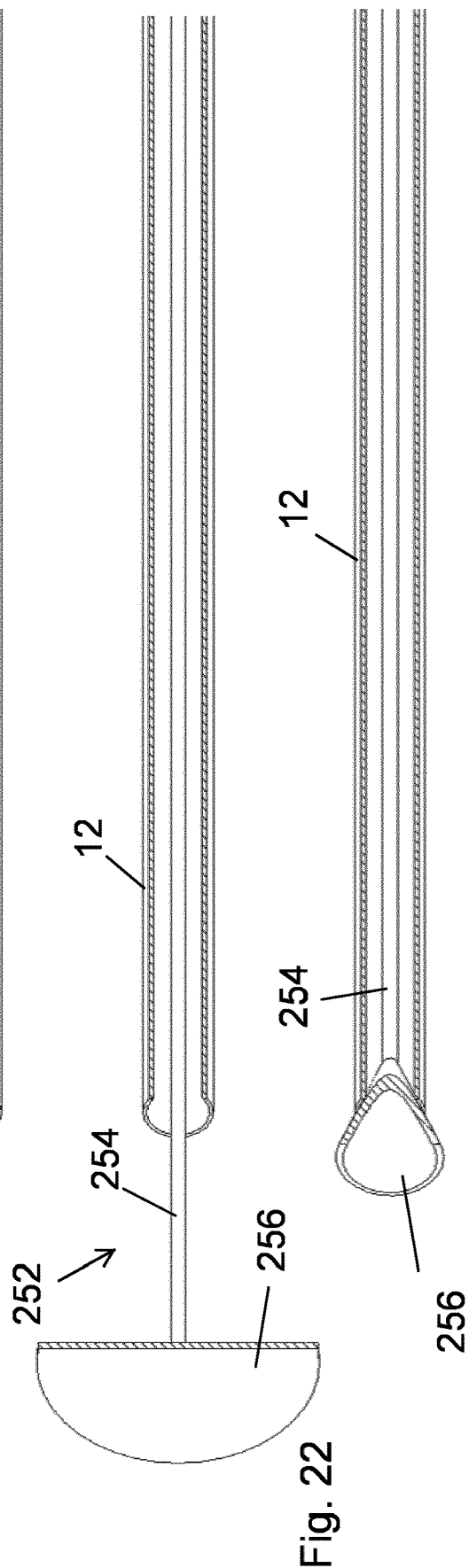

PERCUTANEOUS VASCULAR SURGICAL SYSTEM AND METHOD

This patent application is a 35 U.S.C 371 national stage application of International Patent Application No. PCT/EP2018/062177, filed on May 10, 2018, which claims priority to European Patent Application No. 17170868.8, filed on May 12, 2017. All of these disclosures are hereby expressly incorporated by reference as part of the present disclosure as if fully set forth herein.

FIELD OF THE INVENTION

This invention relates to a percutaneous vascular surgical system and method which provides a simpler yet safer means of performing vascular access, intervention and arterial closure, and is particularly suited to stenting of the carotid artery or neurovascular interventions involving percutaneous access at the neck at a suitable location above the clavicle.

BACKGROUND OF THE INVENTION

Vascular intervention involves any form of surgery to treat diseases or complications of the vascular system including arteries, veins and the lymphatic system and may take many forms, for example angioplasty, insertion of stents, clot retrieval for stroke and heart attack, embolic protection, stroke prevention, brain aneurysm and embolization or the like. Vascular surgery generally involves minimally invasive catheter based procedures which are preferred over open surgery due to reduced complications, reduced physical stress on the patient, reduced recovery time and minimal scarring associated with open surgery.

There are however still complications involved in such minimally invasive vascular surgery, and for example stenting of the carotid artery may involve traditional transfemoral access with distal embolic protection requiring the surgeon to traverse the aortic arch which is associated with a high risk of embolization and intraoperative stroke, and the placement of distal protection devices is also associated with increased embolization during placement and risks vessel damage, dissection and spasms. Transfemoral access via the groin requires the application of significant negative (vacuum) pressures to effect aspiration, due to the significant distances from the aspirator to the surgical site, as the distance results in a large pressure drop along the length of the aspirator line thereby requiring the significant negative pressures. These procedures therefore require complex and costly equipment and often require multiple experienced operators to be present during the procedure to correctly operate and monitor equipment.

Currently there is no system available that allows percutaneous carotid access at the neck for neurovascular interventions. The significance of this is that an interventionalist preferring percutaneous access at the leg or arm risks generating emboli as they cross the aortic arch, which could lead to stroke. On the other hand, a surgeon preferring surgical access at the neck faces a number of significant issues, namely that surgical incision is required, and as the cranial nerves are located in the neck, there is a risk of nerve damage when performing surgery to access the artery. Surgical incisions and dissection give rise to potential wound complications and general anaesthetic is typically utilised. As a result of all of the above the patient typically overnights in hospital and a requires a longer patient recovery time due to the surgical incision. There is also a significant, risk with damaging the cranial nerve of facial paralysis or damage to the voice box, tongue and/or difficulty with swallowing or breathing functions.

It is therefore an objective of the present invention to provide an improved percutaneous vascular surgical system and method, and in particular an improved system and method which is capable of occluding the artery, providing access for vascular intervention, safely removes emboli and incorporates a closure device.

SUMMARY OF THE INVENTION

According to a first aspect of the present invention there is provided a percutaneous vascular surgical system comprising:

a sheath having a proximal end and a distal end and defining a main lumen extending between the proximal and distal ends;

at least one auxiliary lumen defined by the sheath;

a reversibly inflatable first balloon located about the sheath adjacent the distal end and in fluid communication with the auxiliary lumen;

a negative pressure generator selectively connectable to the main lumen; and a vascular closure device operable through the main lumen to seal an opening in a wall of a blood vessel through which vascular access of the sheath is achieved.

Preferably, the auxiliary lumen is disposed concentrically of the main lumen.

Preferably, a sidewall of the sheath is reinforced.

Preferably, the sheath is capable of being preformed.

Preferably, the sheath is angulated adjacent the distal end.

Preferably, the sheath comprises a circumferentially extending annular channel on an exterior of a sidewall of the sheath into which the first balloon, when deflated, is at least partially recessed.

Preferably, the negative pressure generator comprises an at least partially evacuatable reservoir.

Preferably, the negative pressure generator is configured to generate a negative pressure of 50 mmHg or less.

Preferably, the negative pressure generator comprises a manually operable syringe.

Preferably, the system comprises a manually operable valve disposed between the negative pressure generator and the main lumen.

Preferably, the system comprises a port adapted for connection to a blood pressure gauge.

Preferably, the sheath comprises a marker on either side of the first balloon.

Preferably, the sheath is adapted to deliver a sealant from at or adjacent the distal end.

Preferably, the vascular closure device comprises a closure member displaceable between a collapsed and expanded state, and a catheter on which the closure member is mounted to allow the closure member to be delivered through the main lumen.

Preferably, the closure member comprises a second balloon.

Preferably, the vascular closure device comprises a sealant delivery system operable through the sheath to dispense a sealant about an opening in a wall of a blood vessel through which vascular access of the sheath was achieved.

Preferably, the catheter comprises an internal bore through which the sealant may be delivered.

Preferably, the catheter comprises an outlet from which sealant may be dispensed from the internal bore.

Preferably, the catheter comprises a marker adjacent the outlet.

Preferably, the system comprises a plug deliverable through the main lumen.

Preferably, the plug is deliverable over and along the catheter.

According to a second aspect of the invention there is provided a vascular closure device comprising a closure member displaceable between a collapsed and expanded state, and a catheter on which the closure member is mounted to allow the closure member to be delivered through a lumen in a surgical device to an opening in a blood vessel.

Preferably, the closure member comprises a second balloon.

Preferably, the closure device comprises at least one marker on the catheter to facilitate identification of the position of the second balloon.

Preferably, the device comprises a sealant delivery system operable to dispense a sealant adjacent a proximal side of the balloon.

Preferably, the device comprises a plug deliverable along the catheter to a proximal side of the closure member.

Preferably, the device comprises a plurality of graduated visible markers on an exterior of the catheter.

According to a third aspect of the invention there is provided a method of vascular surgery comprising the steps of percutaneous insertion of a multi lumen sheath into a blood vessel; inflating a first balloon located about a distal end of the sheath in order to occlude the blood vessel; performing a surgical procedure within the blood vessel via the sheath; generating suction through the sheath during the surgical procedure; deflating the first balloon; prior to removing the sheath from the blood vessel, passing a vascular closure device through the sheath; withdrawing the sheath from the blood vessel; and sealing an opening in the blood vessel through which the sheath was inserted with the vascular closure device.

Preferably, the method comprises passing a closure member of the vascular closure device through the sheath into the blood vessel; expanding the closure member from a collapsed state; withdrawing the sheath from the blood vessel with the closure member remaining in the blood vessel; and drawing the closure member against the opening.

Preferably, the method comprises the step of extravascular application of a sealant about the opening via the sheath.

Preferably, the method comprises the step of delivering a plug through the sheath and depositing the plug in or adjacent to the sealant.

Preferably, the method comprises the step of collapsing the closure member and withdrawing the closure member from the blood vessel via the opening.

Preferably, the method comprises the step of applying manual compression against the opening.

Preferably, the method comprises utilising a negative pressure of 50 mmHg or less in order to generate the suction, and effect a reversal of flow.

Preferably, the method comprises the step of effecting the reversal of blood flow in the vessel and surrounding vessels through the application of the negative pressure in order to assist in organ perfusion and/or emboli removal during the vascular intervention.

According to a fourth aspect of the invention there is provided a method of percutaneous closure of an opening in a blood vessel comprising the steps of delivering a collapsed closure member through the opening into the blood vessel; expanding the closure member; drawing the closure member against the opening; extravascular application of a sealant about the opening; collapsing the closure member; and withdrawing the closure member from the blood vessel through the opening.

Preferably, the method comprises the step of delivering the sealant through a catheter on which the closure member is mounted.

Preferably, the method comprises the step of depositing a plug in or adjacent the extravascular sealant.

Preferably, the method comprises delivering the plug along the catheter.

As used herein, the term "proximal" is a relative term intended to mean an end or part of a component or a location that is closer or closest to the user or operator with respect to another part or location.

As used herein, the term "distal" is a relative term intended to mean an end or part of a component or a location that is further or furthest from the user or operator with respect to another part or location.

As used herein, the term "upstream" is a relative term intended to indicate a position of one item or location relative to another item or location with respect to a direction of flow of a fluid, such as blood, and means that the item or location in question is separated by a distance travelled against or in the opposite direction to the fluid flow.

As used herein, the term "downstream" is a relative term intended to indicate a position of one item or location relative to another item or location with respect to a direction of flow of a fluid, such as blood, and means that the item or location in question is separated by a distance travelled with or in the direction of the fluid flow.

BRIEF DESCRIPTION OF THE DRAWINGS

The present invention will now be described with reference to the accompanying drawings, in which;

FIG. 20 illustrates a cross sectional view of an alternative embodiment of a closure device according to the invention;

FIG. 21 illustrates a cross sectional view of a further alternative embodiment of a closure device 30 according to the invention and in a collapsed state for delivery into an artery;

FIG. 22 illustrates the closure device of FIG. 21 in an expanded state to effect closure of a puncture in an artery; and FIG. 23 illustrates the closure device of FIGS. 21 and 22 in a retracted state for removal from the artery.

DETAILED DESCRIPTION OF THE DRAWINGS

Figure 1:
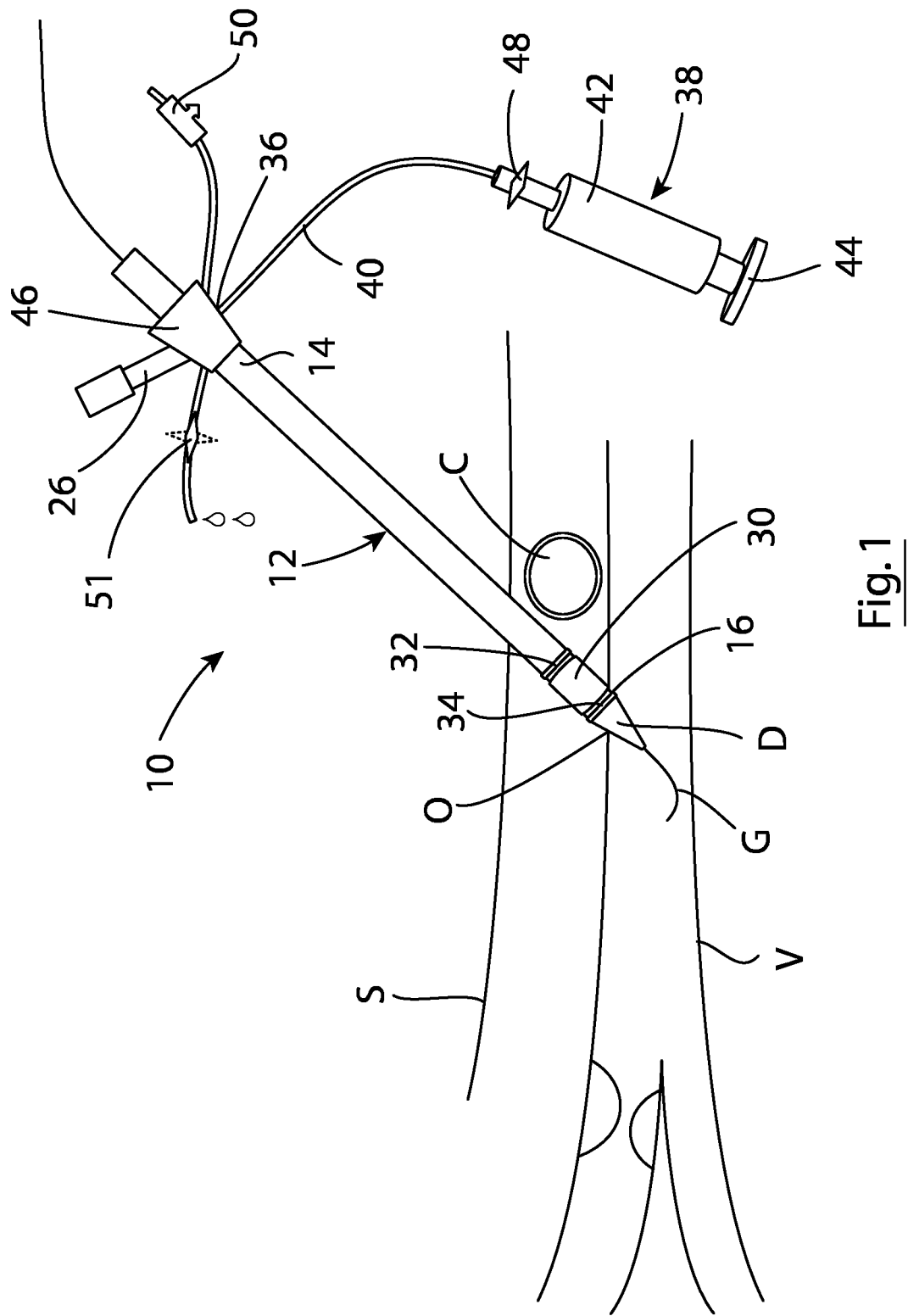
FIG. 1 illustrates a schematic representation of an exemplary embodiment of a percutaneous vascular surgical system according to the present invention being inserted into the common carotid artery as an example of a cannulated artery.

Referring now to the accompanying drawings there is illustrated a percutaneous vascular surgical system according to a preferred embodiment of the present invention, generally indicated as 10, and having use in a percutaneous endovascular/neurovascular interventional method according to the present invention and which may be used to perform vascular surgery at and from various sites. For example the vascular surgical system 10 may be used to perform vascular surgery within, or gain access via, the brachial, femoral, carotid, radial, ulnar, axillary or other blood vessels. The system 10 and method of the invention may be used to access the carotid artery for internal or common carotid artery stenosis, to access the heart for angioplasty and clot retrieval, access to the brain for middle cerebral arteries for aneurysm coiling or clot retrieval, for M1 or A1 intra cerebral revascularisation for stroke, access to the kidneys for renal arteries and access to the bowel for superior mesenteric artery revascularisation. The surgical system 10 can be used for surgical procedures such as angioplasty, stenting, clot retrieval for stroke or heart attack, embolic protection, stroke prevention, brain aneurysm embolization, uterine embolization, angiodysplasia embolization in the bowel for bleeding, varicocele embolization, tumour embolization, visceral aneurysm embolization and any other suitable procedures. As will be described in greater detail hereinafter, the surgical system 10 is substantially comprised of readily available and low cost components which will thus ensure that the cost and complexity of the system 10 remains extremely competitive, while the operation thereof is straightforward and can be essentially fully operated by a single surgeon and with relatively little training, rendering the system 10 extremely attractive for hospitals, as it reduces costs by increasing outpatient treatment, avoids the need for a general anaesthetic, and lowers the risk of wound complications and in the case of procedures involving the carotid artery, significantly lowers the risk of cranial nerve damage.

The surgical system 10 comprises an elongate cylindrical sheath 12 which may be formed from any suitable material or composite of multiple materials, and may be reinforced internally or externally, for example by coiling, braiding, ribbing or any other suitable functional alternative. In addition the sheath 12 may be fully rigid, partially or fully flexible in the longitudinal direction while being substantially incompressible radially, straight, angled, comprise a hooked or curved end, and may be actively steerable as is known in the art, or may be locally flexible in order to allow deformation during insertion of the sheath 12. In a particularly preferred embodiment the sheath 12 is comprised of coil reinforced enhanced kink resistant coaxial tubing, and may be formed from a material such as a Pebax® MED elastomer or other polymer of similar physical characteristics. The reinforced yet malleable construction of the sheath 12 allows the proper cannulation of the carotid artery, with suitable angulation of the sheath 12 allowing the system 10 to access the carotid artery by means of percutaneous entry from a position on the neck of the patient above the clavicle C, significantly reducing the length of artery to be traversed in order to reach the surgical site, thereby reducing surgery times, risk of embolization, and thus improve patient experience. The length and diameter of the sheath 12 may be varied as required. However, as set out in further detail hereinafter, the system 10 is primarily designed for percutaneous cervical access to the carotid artery for neurovascular intervention and as a result the sheath 12 and related components of the system 10 can be made significantly shorter than equivalents designed for more conventional transfemoral access.

The sheath 12 has a proximal end 14 and an opposed distal end 16 extending between which is a main lumen 18 via which various aspects of the surgical procedure of the present invention may be performed as hereinafter described in detail. In a particularly preferred embodiment the sheath 12 is of sufficient length such that the surgeon does not have to have their hands under the fluoroscope during the surgical procedure. The sheath 12 may be peelable in order to facilitate deployment of additional components of the surgical system 10 as hereinafter described in detail and when intended for use in carotid artery stenting or similar procedures involving percutaneous access via the neck, may be angulated, with an angle of between 100 and 160 degrees, most preferably approximately 135 degrees. In the exemplary embodiment illustrated the sheath 12 has a diameter of 7 Fr and an overall length of approximately 350 mm. The distance between the distal end 16 and the elbow is approximately 15 mm and the distance from the elbow to the proximal end 14 is approximately 200 mm. It will of course be appreciated that these dimensions and angles may be varied as required.

Figure 17:
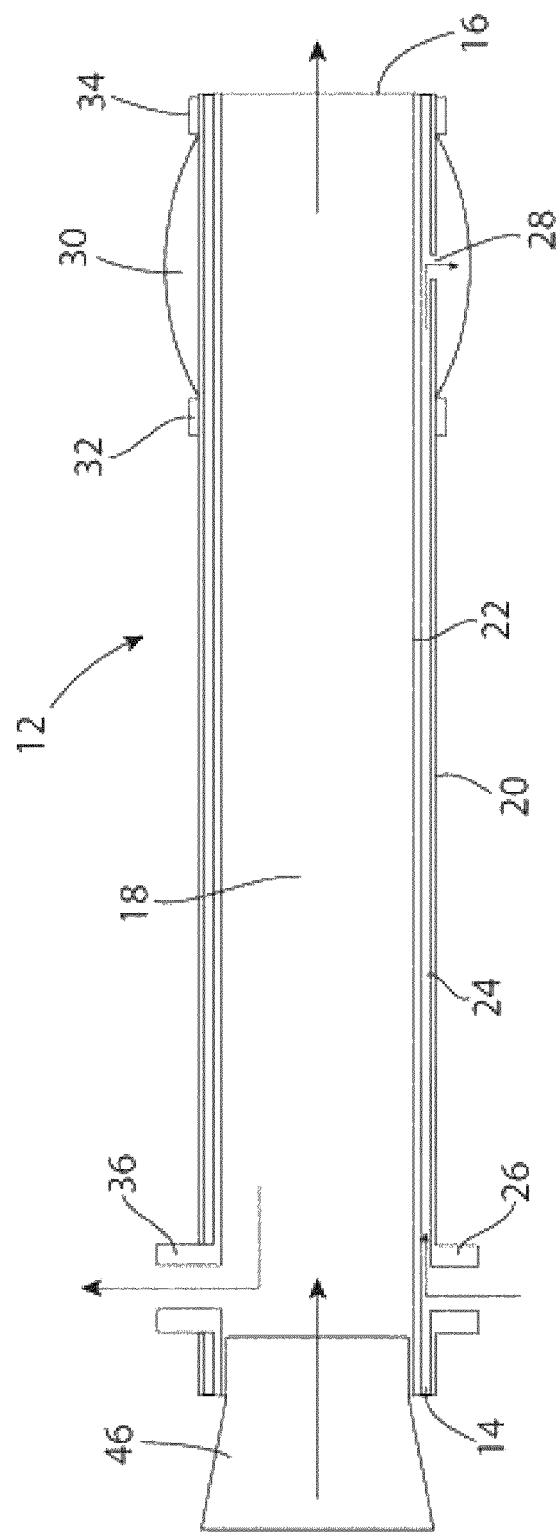
FIG. 17 illustrates a schematic sectioned view of one possible embodiment of the sheath of the vascular surgical system of the present invention.

In the preferred embodiment illustrated the sheath 12 is of double wall construction, having an outer wall 20 and an inner wall 22 spaced therefrom such as to define an auxiliary lumen 24, as shown in the sectioned view of FIG. 17. The auxiliary lumen 24 is accessible via a first port 26 adjacent the proximal end 14 of the sheath 12, the auxiliary lumen 24 extending approximately the full length of the sheath 12 to an aperture 28 in the second wall 22 and adjacent but a short distance from the distal end 16 of the sheath 12. The surgical system 10 comprises a first balloon 30 circumscribing the sheath 12 adjacent the distal end 16 and overlying the aperture 28 such that the first balloon 30 may be inflated by pumping a fluid such as a saline solution or other solution through the first port 26 and the auxiliary lumen 24 into the first balloon 30. When inflated within an artery such as the common carotid artery the first balloon 30 has a diameter or size sufficient to allow the balloon 30 to effect endoclamping, in order to completely occlude the artery and therefore prevent blood flow past the balloon 30 as hereinafter described. In the exemplary embodiment illustrated, having particular use for carotid artery stenting, the balloon 30 has an approximate diameter of 15 mm when inflated, although it will be understood that as the balloon 30 is compliant is will continue to expand until it conforms to the inner wall of the vessel in question such as to effect complete occlusion of the vessel. The balloon 30 is positioned immediately adjacent the distal end 16 such that when inflated it creates a occlusion within the artery or other vessel while leaving the open distal end 16 fully exposed or uncovered, allowing fluid flow through the main lumen 18 via the distal end 16 in order to effect aspiration of the artery or other vessel as will be described.

Similarly, the first balloon 30 may be deflated by evacuating said fluid along the above-mentioned path. Any suitable supply (not shown) of such a fluid may be connected to the first port 26 during the operation of the surgical system 10 and as will be described in greater detail hereinafter. The sheath 12 preferably comprises a circumferentially extending annular channel (not shown) formed in the exterior of the sidewall and in which the balloon 30, when deflated, is at least partially recessed. This reduces the post deflation profile of the distal end 16 in order to prevent dissection or injury to the artery on removal of the sheath 12.

The first port 26 may be provided with any suitable coupling such as a threaded coupling thereon to enable the fluid tight connection of the fluid supply for the inflation of the first balloon 30. The first balloon 30 may be formed from any suitable compliant or non-compliant material, preferably latex free, and for example a polyblend material or polyurethane material, and is located between a pair of radiopaque markers, a proximal marker 32 and a distal marker 34 in order to allow the position of the first balloon 30 and the distal end 16 of the sheath 12 to be visualised under a fluoroscope during the surgical procedure. In the exemplary embodiment illustrated the distal marker 34 is located 2 mm from the distal end 16 and the proximal marker 32 is located 15 mm from the distal end. While radiopaque markers are the preferred form of marker, any other suitable marker may be employed. In addition, the entire length of the sheath 12 may be provided with markers, preferably radiopaque markers, in order to delineate the sheath when viewed through a fluoroscope of other imaging equipment, so as to allow accurate positioning of the sheath 12 during the various stages in the surgical procedures to be undertaken with the system 10 of the invention, in order to correspond to the predetermined positions established through pre-operative planning and based on CT scan measurements of the patient. The sheath 12 may also include a sliding or otherwise displaceable marker (not shown) located externally, preferably circumferentially of the sheath 12, to enable a determination and recordal of the depth of the artery or other vessel from the skin surface.

While the main lumen 18 and auxiliary lumen 24 are disposed concentrically of one another in the preferred embodiment of the sheath 12, it will of course be understood that any other suitable arrangement and placement of the lumens 18, 24 may be employed, for example a tube in tube arrangement or the like, or with the auxiliary lumen located on an exterior of the sheath 12. It will also be appreciated that the exact location of the first balloon 30 relative to the distal end 16, and the exact location of the proximal and distal markers 32, 34 may be varied without departing from the scope and functionality of the invention.

In addition to access to the main lumen 18 via the proximal end 14 of the sheath 12, a second port 36 is additionally provided, exiting laterally from the sidewall of the sheath 12 which provides secondary access to the main lumen 18. It will be understood that the exact location, size and orientation of the second port 36 may be varied while retaining the necessary functionality of providing access to the main lumen 18, in particular where the arrangement of the main lumen 18 and auxiliary lumen 24 vary to that of the preferred embodiment illustrated. As with the first port 26, the second port 36 may have any suitable form of coupling or connector formed or provided thereon in order to facilitate the establishment of a fluid tight connection to the second port 36.

The surgical system 10 additionally comprises a negative pressure generator in the form of a syringe 38 connected to the second port 36 via a suitable length of tubing 40. It will be appreciated that any other suitable connection between the syringe 38 and the second port 36 may be provided to establish fluid communication between the syringe 38 and the main lumen 18, and that any other functional equivalent to the syringe 38, for creating suction or negative pressure, may be employed. The syringe 38 is preferably of conventional form having a cylindrical body 42 displaceable relative to which is a plunger 44 which may be withdrawn outwardly of the body 42 in order to generate suction or negative pressure in the interior volume of the body 42 in conventional fashion. During use of the surgical system 10 this suction or negative pressure will thus be transmitted via the main lumen 18 to the distal end 16 of the sheath 12, the proximal end 14 being sealed by a suitable conventional haemostatic valve 46 which provides a fluid tight seal at the proximal end 14 while permitting the passage of surgical devices such a guide wires, catheters and the like while maintaining said seal. This suction, as described hereinafter, is utilised to establish reverse blood flow in the blood vessel in which surgery is being performed in order to locally withdraw blood and any emboli from about the surgical site. The syringe 38 or other negative pressure generator is preferably operable to generate a negative pressure of 50 mmHg or less in order to avoid, in use, brain hypoperfusion. By understanding this important requirement it was possible to use the simple syringe 38 to effect aspiration and so benefit from the simplified operation and reduced cost of the syringe 38. The reversal of blood flow generated by the syringe 38 draws blood from the surrounding blood vessels in order to maintain organ perfusion and emboli removal through flow reversal during the procedure. Due to the significantly shortened access path to the surgical site, in the case of percutaneous access via the neck to the carotid artery, the surgical time is very significantly reduced and as a result only a relatively small quantity of blood is required to be aspirated via the syringe 38, and thus the system 10 does not require reintroduction of the aspirated blood, thereby avoiding the requirement for filtering of the blood and complex additional apparatus to effect reintroduction to the patient. This again significantly reduces the operative time, the complexity and cost of the procedure, further improving patient experience over conventional systems.

Disposed between the second port 36 and the syringe 38 is a valve 48 which is preferable manually operable in order to allow the surgeon to open and close the valve as required in order to selectively establish suction through the main lumen 18. In practice and as will be described in greater detail hereinafter, the valve 48 is closed and the plunger 44 drawn outwardly of the body 42 such as to create a vacuum or negative pressure within the body 42. The syringe 38 is preferably configured to generate a negative pressure of no more than 50 mm Hg. Then, when suction is required, it is a simple matter for the surgeon to manually open the valve 48 for the selected period of time that suction is required, namely while the surgical procedure is being performed and thus while emboli may be created, and to then close the valve 48 once the procedure is complete and the risk of emboli is removed. In a particularly preferred embodiment the syringe 38 is adapted to allow the plunger 44 to be locked at incremental distances of withdrawal from the body 42 so that the plunger does not creep back into the body under the influence of the vacuum established within the syringe 38. Such syringes are well known in the art and readily available, and thus no further explanation on the configuration and operation of same is deemed necessary.

The surgical system 10 preferably additionally comprises a port 50 adapted for connection to a blood pressure gauge, or a fractional flow reverse wire (not shown) disposed between the syringe 38 and the second port 36 in order to allow monitoring of blood pressure during the surgical procedure performed using the system 10 of the invention, again as will be described hereinafter.

The surgical system 10 preferably additionally comprises an additional port from the haemostatic valve 46 connected by means of tubing to a valve 51, which by opening pulsatile blood flow can be detected. The port 50 for connection to the blood pressure gauge may alternatively or additionally be located on this branch of tubing. The drawings generally show both options for completeness but it will be understood that this is not essential to the operation of the invention.

Figure 8:
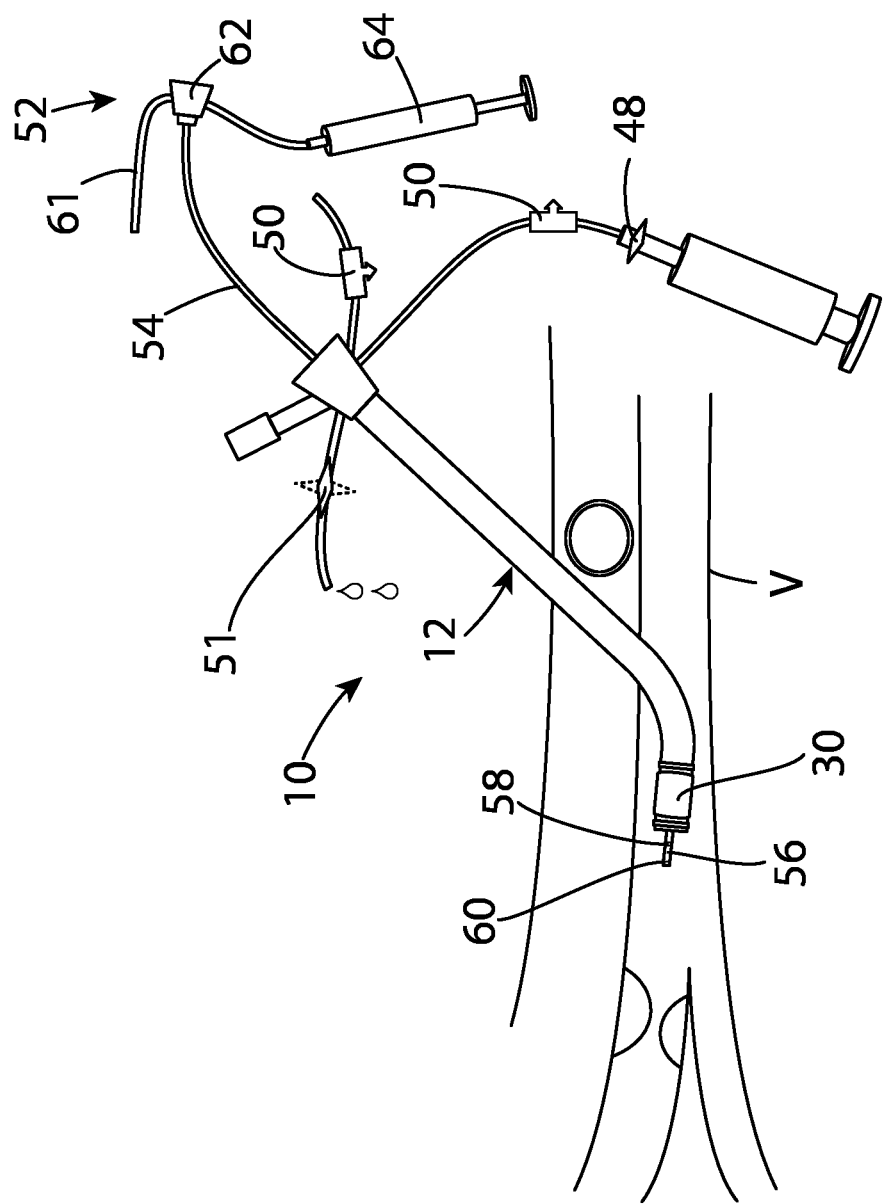
FIG. 8 illustrates the initial insertion of a vascular closure device forming part of the vascular surgical system of the invention.
Figure 19:
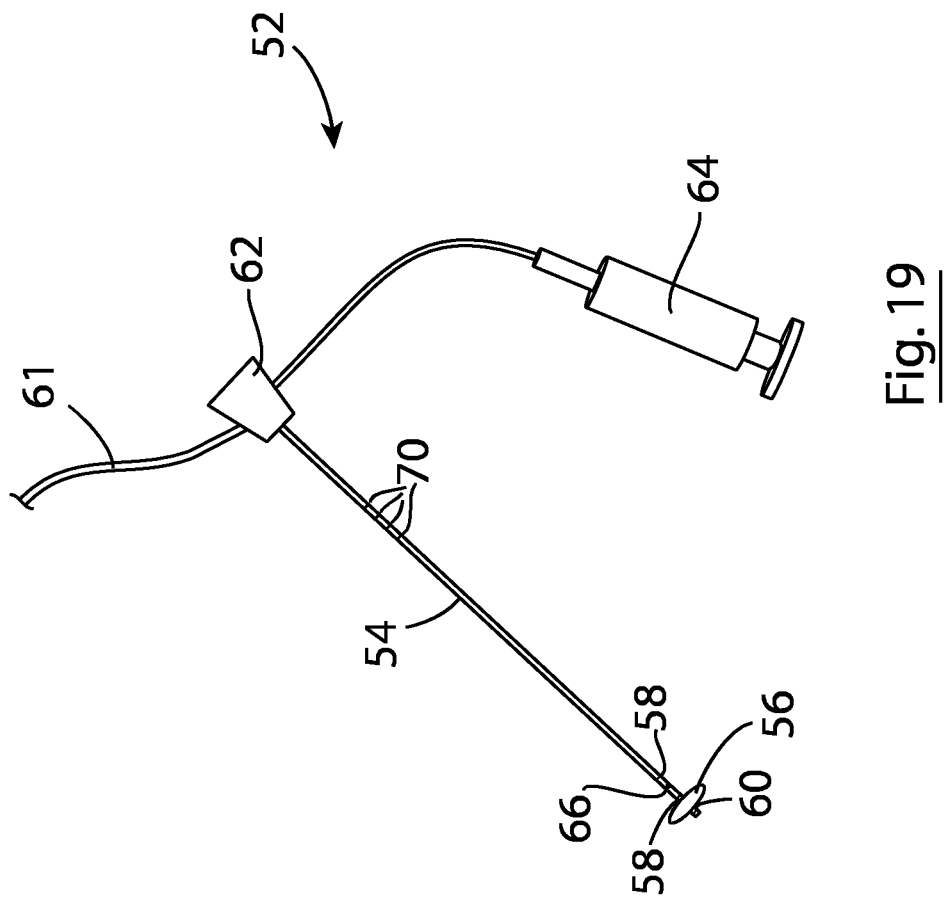
FIG. 19 illustrates a schematic representation of the vascular closure device shown in FIGS. 8 to 14 in isolation from the vascular surgical system.

Referring now to FIG. 8, the surgical system 10 of the present invention further comprises a vascular closure device 52 which is operable via the sheath 12 in order to close an opening O in a blood vessel V in which the vascular surgical procedure is performed, following withdrawal of the sheath 12 at completion of the procedure. The vascular closure device is illustrated in isolation in FIG. 19, with alternative embodiments shown in FIGS. 20 and 21 to 23. The vascular closure device 52 is operable through the sheath 12, thereby further simplifying the entire procedure by allowing all of the operations of the entire procedure to be performed with a single system 10. The vascular closure device 52 comprises a multi lumen catheter 54 comprising a closure member in the form of a second balloon 56 disposed circumferentially about a distal end of the catheter 54, the second balloon 56 being positioned between a pair of radiopaque markers, a proximal marker 58 and a distal marker 60, again to allow the position of the second balloon 56 to be visualised during the surgical procedure by means of a fluoroscope. Again, it will be understood that any other combination of radiopaque markers, such as a marker under the second balloon 56, or any other suitable functional alternative to a radiopaque marker may be employed. A graduated number of visible markers 70 may also be employed on the shaft of the catheter 54, as illustrated in FIG. 19, in order to allow the determination of the precise location of the second balloon 56 relative to the sheath 12.

The second balloon 56 is inflatable via one of the lumens within the catheter 54, through which a fluid such as saline may be pumped via an inflation line 61 connected to a manifold 62 at the proximal end of the catheter 54. Any suitable source of pressurised fluid may be suitably connected to the manifold 62 in known fashion.

The vascular closure device 52 additionally comprises a sealant delivery system in the form of a conventional syringe 64 filled with a known vascular sealant and connected via the manifold 62 to the second lumen within the catheter 54, which lumen terminates at an outlet 66 at the proximal side of the second balloon 56 such that the vascular sealant may be pumped from the syringe 64 through the catheter 54 to be dispensed out of the catheter 54 about the proximal side of the second balloon 56. A marker 67 may be provided on the catheter 54, at the proximal side of the outlet 66, in order to allow the position of the outlet 66 to be determined during use. Alternatively the vascular sealant may be delivered by any other suitable means and/or route, for example via an alternative lumen (not shown) in the sheath 12, or through the main lumen 18 in the sheath 12. The vascular sealant may be of any suitable form and/or composition, and may for example comprise a fibrin based material and may be in the form of a hydrogel or other biocompatible material which is preferably capable of swelling to multiple times the original volume in order to fully occlude the opening O in the vessel V.

The catheter 54 may comprise additional lumens, for example to deliver an activator composition separate to the sealant, for mixing with the sealant at the arteriotomy site. In that case the vascular closure device 52 may comprise a further syringe (not shown) or functional equivalent, such as a double barrelled syringe, for dispensing the activator. The use of the term "sealant" should however be understood to cover a sealant, a combination of a sealant and activator, or indeed an activator in isolation.

The vascular closure device 52 additionally comprises a vascular plug 68 which is adapted to be delivered to the arteriotomy site, for example by being threaded onto and along the catheter 54 and dimensioned to pass through the main lumen 18 of the sheath 12 such that the vascular plug 68 may be delivered through the sheath 12 to the opening O in the blood vessel V, as will be described in detail hereinafter. Alternatively the vascular plug 68 may be delivered by any other suitable means and/or route, for example via an alternative lumen in the sheath 12, or via one of the lumens in the catheter 54. The vascular plug 68 may be of any suitable size and shape, and may be selected from any one of a number of commercially available vascular plugs, and may for example take the form of a pledget comprising a hydrogel material or like. Closure of the arteriotomy site may also be achieved by means of any other suitable commercially available system, for example a clip or staple based system including but not limited to a StarClose® or PerClose® closure device.

While the vascular closure device 52 is described as an integral part of the surgical system 10 and method of the present invention, it will be understood from the following description of operation that the vascular closure device 52 could be used as a stand alone means of vascular closure and may thus find uses separate from the surgical system 10 and method, to be used with other systems or as a self contained vascular closure system and method. It will also be understood that the second balloon 56 may be replaced with any other functional alternative which may be displaced between a collapsed and expanded state, and could for example take the form of a disk of material mounted on a suitable support and collapsible relative to the support in the manner of an umbrella.

An exemplary embodiment of the surgical system 10 and method of the present invention will now be described as applied to a surgical treatment of a blocked carotid artery (carotid stenosis), a disease which causes 5.5 million fatalities each year worldwide. However, as hereinbefore described, the surgical system 10 of the present invention can be used in a large number of other procedures, and the use for carotid stenosis is merely an exemplary application of the system 10 and method of the present invention, but one which has an added complication to access at the cervical area to the carotid artery due to the obstruction caused by the clavicle C. In addition the exact number and sequence of steps may vary from procedure to procedure, in particular the timing and frequency of generating suction using the syringe 38.

The design and operation of surgical system 10 of the present invention allows percutaneous access to the vascular system, and in the exemplary application hereinafter described, at the neck of the patient, which allows for a faster, safer and more cost-effective means of treating carotid stenosis or other vascular issues. In addition, the surgical method of the present invention does not require a surgical incision with a blade, but rather a small puncture in the neck above the clavicle C or other location, thus avoiding scarring of the neck or elsewhere. However in order to achieve this functionality there were a number of obstacles to be overcome by the surgical system 10 and method of the invention, in particular to temporarily block the carotid or other artery or vessel in order to stop ante grade blood flow during the surgical procedure and encourage retrograde reverse flow to enhance brain perfusion, the removal of emboli which could otherwise cause a stroke, the deployment of a stent through the system 10 for treatment of carotid artery disease, and the closure of the artery on completion of the operation.

Turning then to FIG. 1 the skin S and vessel V are initially punctured with a conventional cannulated needle (not shown) to create an opening O in the vessel V, through which a conventional guide wire G is inserted into the vessel V, following which the cannulated needle is removed while leaving the guidewire in place. A dilator D, which carries the sheath 12 is passed over the guidewire and inserted through the skin S into the vessel V as shown in FIG. 1. Advance of the dilator D into the opening O will dilate the opening O to allow the passage of the distal end 16 of the sheath 12. During this procedure the first balloon 30 is in the deflated state, preferably at least partially recessed with a circumferentially extending annular channel (not shown) on the exterior of the sidewall of the sheath 12, and the valve 48 is closed. The proximal and distal markers 32, 34 allow the surgeon to locate the position of the distal end 16 of the sheath 12 and to establish via a fluoroscope or other imaging equipment that the distal end 16 has entered the blood vessel V.

Figure 2:
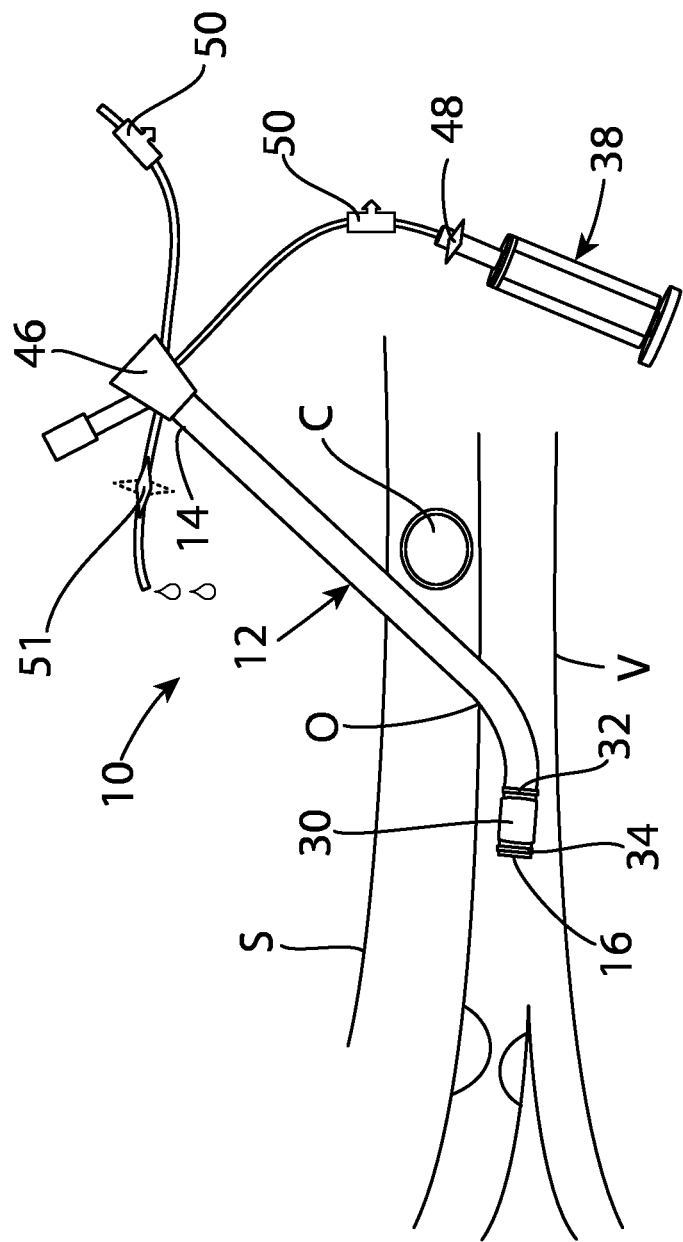
FIG. 2 illustrates the surgical system of FIG. 1 with a dilator removed following insertion of a sheath which forms part of the system into the carotid artery.

Turning then to FIG. 2, the dilator D and guidewire G are withdrawn from the sheath 12. In the case of vascular surgery of the carotid artery with access at the neck, in order to facilitate entry to the blood vessel V above the clavicle C the sheath 12 may be angulated adjacent the distal end 16, or may be flexible or steerable at the distal end 16 in order to achieve the desired shape to facilitate entry at this location. In the exemplary embodiment illustrated the sheath 12 is angulated at a location adjacent the distal end 16 at an angle of approximately 135 degrees. The proximal marker 32 and distal marker 34 can be used under the fluoroscope to allow the surgeon to ascertain that the entire length of the first balloon 30 is sufficiently inserted into the blood vessel V before continuing with the surgical procedure. It will however be understood that the sheath 12 may not be angulated and alternatively may be sufficiently malleable or deformable to conform to the vessel while providing stability for the various interventional components delivered through the sheath 12.

Figure 3:
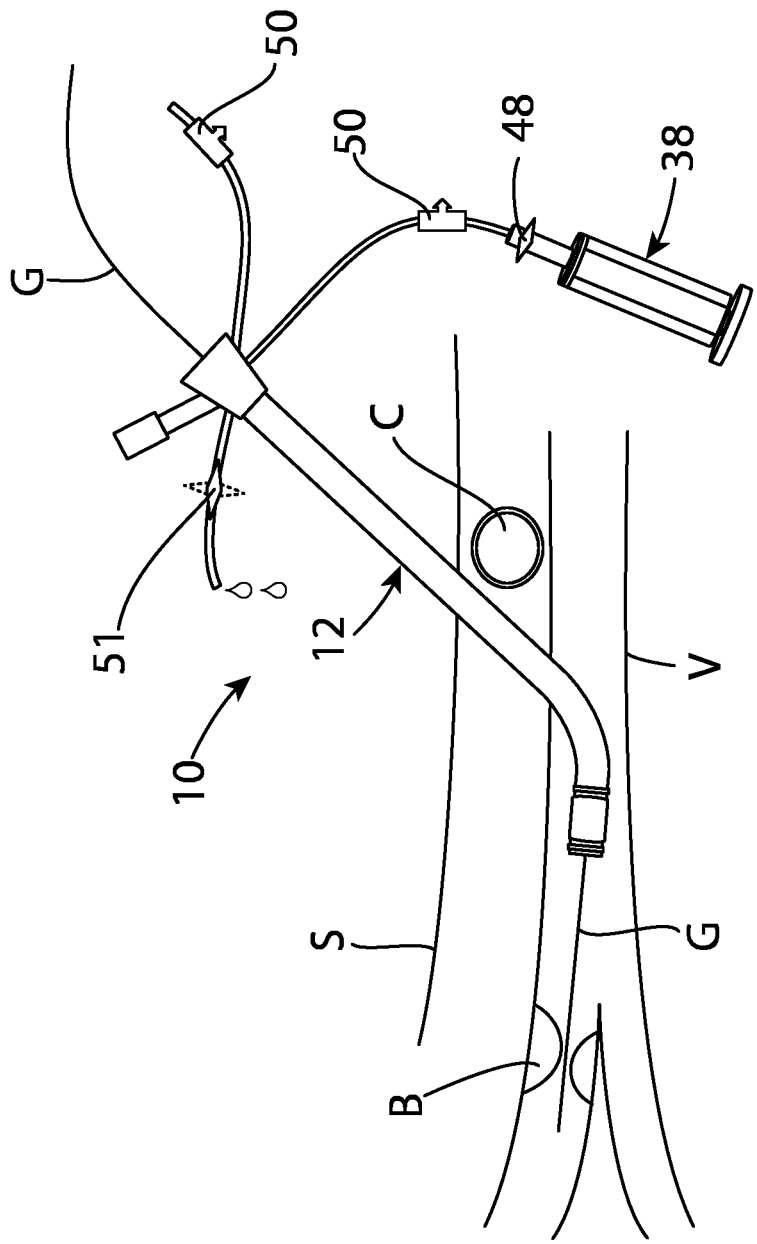
FIG. 3 illustrates the insertion of a guide wire to facilitate the delivery of a device such as a stent into the carotid artery.

Turning to FIG. 3, a guide wire G is the passed through the haemostatic valve 46 and down the main lumen 18 to exit the distal end 16 of the sheath 12 to enter the blood vessel V and be advanced towards the site at which the surgical procedure is to be performed, in this case a partial blockage B of the carotid artery. The guide wire G is thus advanced through and slightly past the blockage B in order to facilitate the insertion of a stent in conventional fashion.

Figure 4:
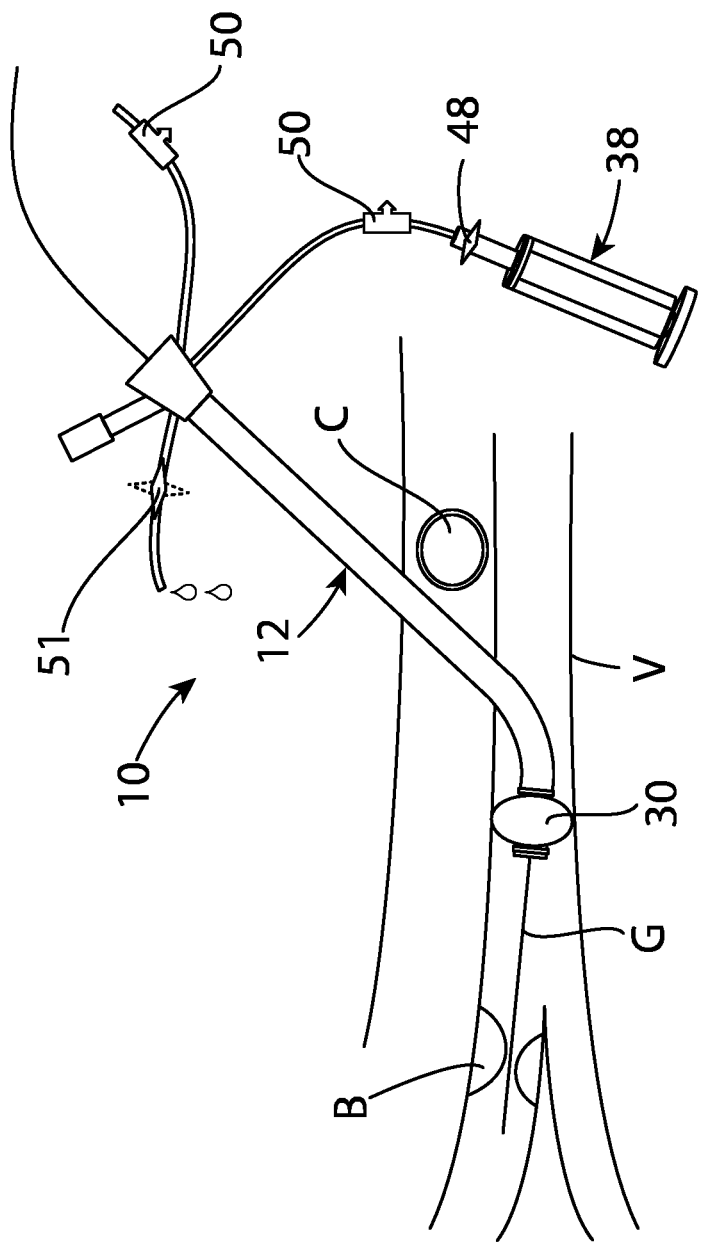
FIG. 4 illustrates the inflation of a first balloon to occlude blood flow in the carotid artery.
Figure 5:
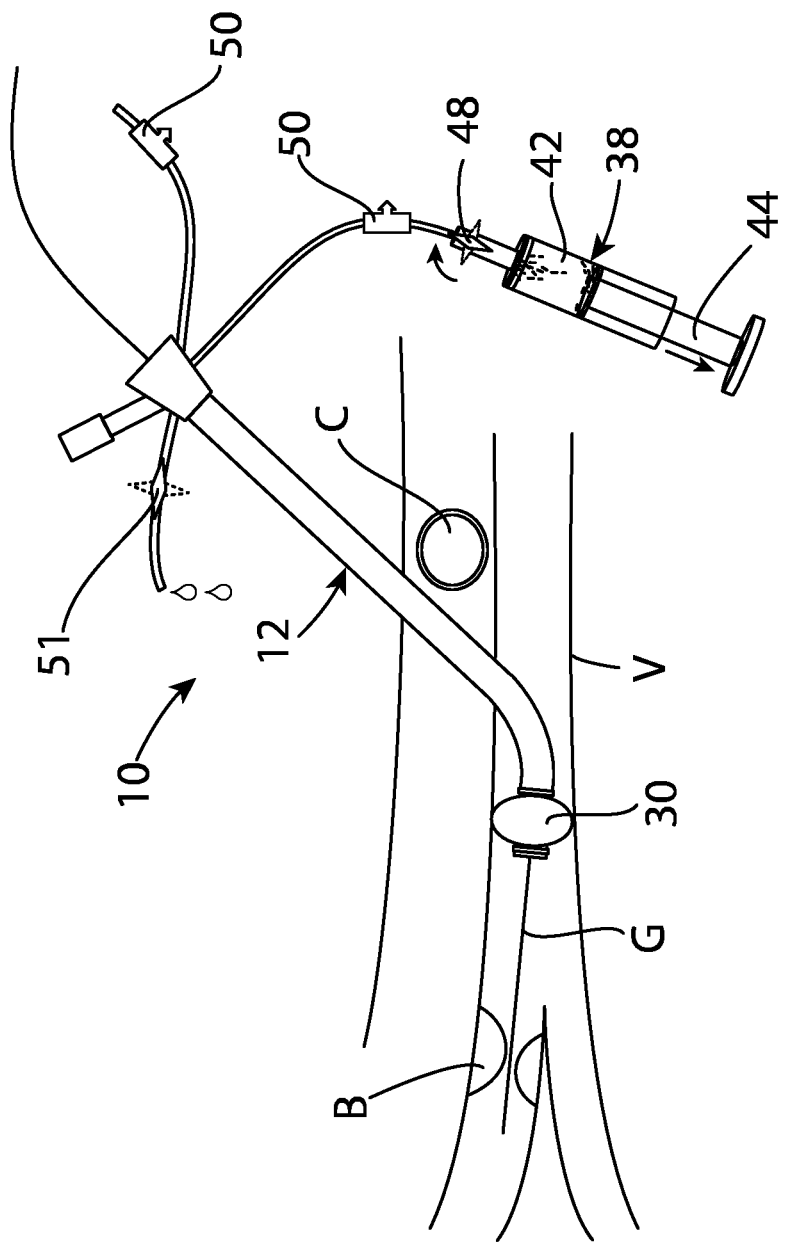
FIG. 5 illustrates the creation of suction to establish reverse blood flow in the carotid artery.

Turning then to FIG. 4, at this point in the procedure the first balloon 30 is inflated, either by the introduction of a saline solution other fluid through the first port 26, thereby inflating the first balloon 30 to block the common carotid artery and thus occlude blood flow during the stenting or other surgical procedure. The location of the first balloon 30 immediately adjacent the distal end 16 allows the vessel V to be completely occluded while leaving the distal end 16 completely open and thus providing unhindered communication between the upstream section of the vessel V and the main lumen 18. Referring to FIG. 5, at this point in this procedure, with the valve 48 in the closed position, the plunger 44 is withdrawn outward from the body 42 of the syringe 38 in order to generate negative pressure or partial vacuum within the syringe 38. Then as the stent or other device is passed through the main lumen 18 of the sheath 12 and into the carotid artery the valve 48 can be manually opened by the surgeon in order to create suction within the main lumen 18 and thus establish retrograde flow from the vessel V into the main lumen 18 in order to effect the removal of blood from around the surgical site, which will thus carry away any emboli generated by the introduction and deployment of the stent or other device at the site of the blockage B through the sheath 12 and into the syringe 38. The low negative pressure generated by the syringe 38 is sufficient, partially due to the relatively short length of the sheath 12, to effect aspiration of the blood while also avoiding brain hypoperfusion. According to Poiseuilles Law, pressure in a tube is inversely related to the $4^{th}$ power of the radius of the tube and directly to the length. Thus for example a tube have a length of 50 cm as opposed to 150 cm, will need significantly less negative pressure, which would therefore allow a smaller tubing radius to achieve equivalent negative pressure. As only a single occlusion of the vessel V is present, the surrounding collateral arteries remain open and so are recruited to assist in organ perfusion throughout the surgical procedure.

Figure 6:
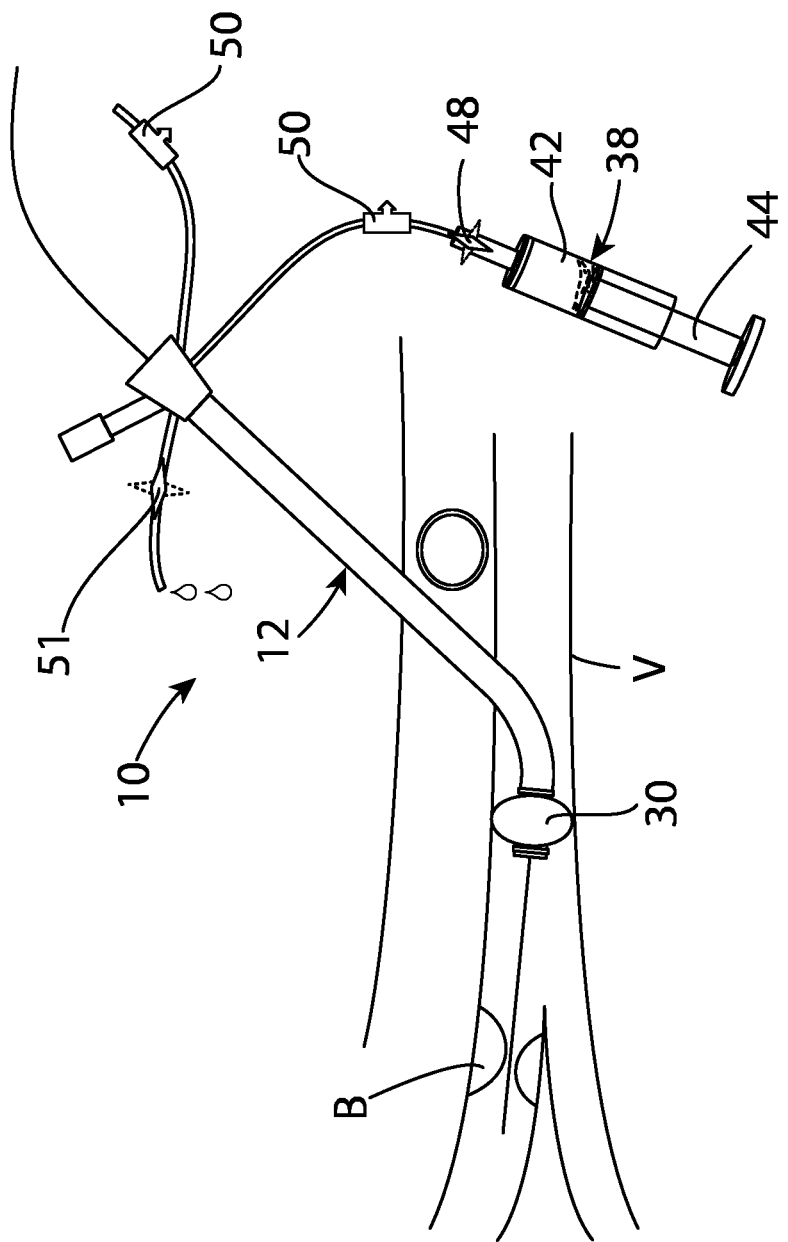
FIG. 6 illustrates a schematic representation of a vascular surgical procedure being performed by the surgical system of the invention including inflation of an occluding balloon and the generation of reverse suction by means of a syringe forming part of the surgical system.
Figure 7:
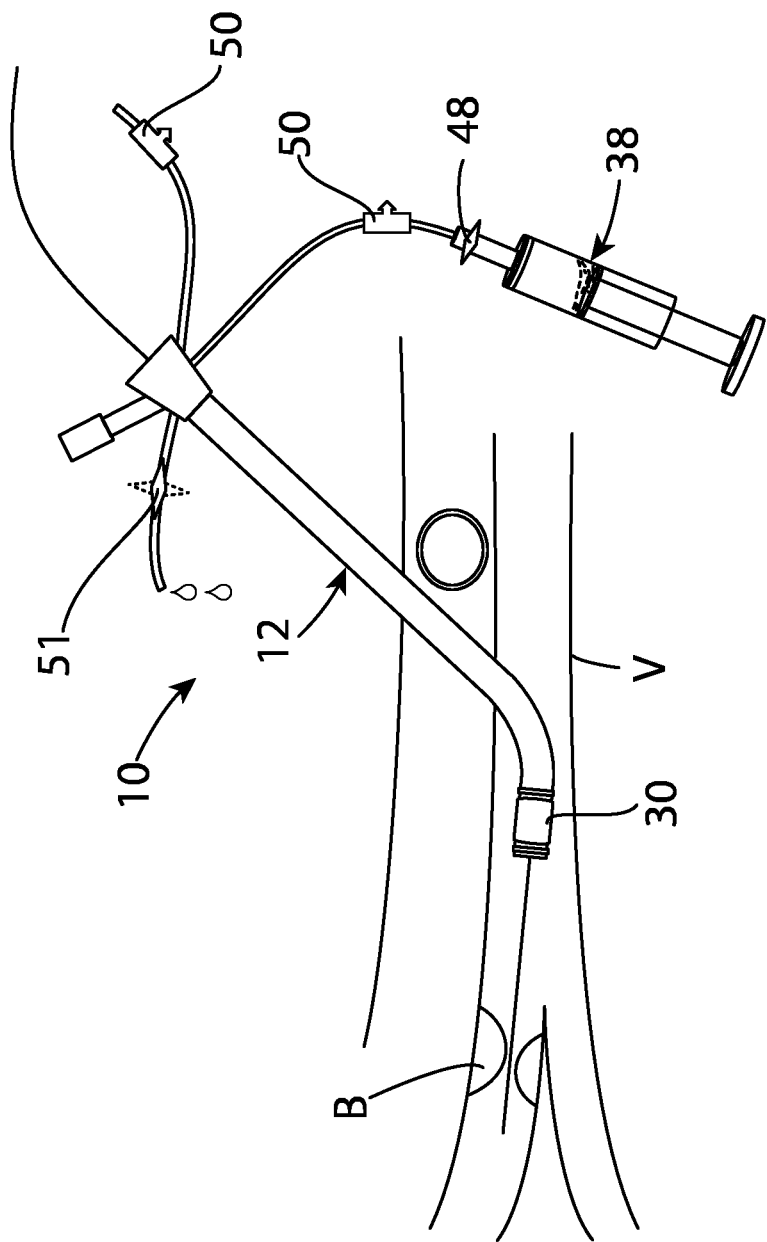
FIG. 7 illustrates deflation of the first balloon following completion of the vascular surgical procedure.

Turning to FIG. 6, once the stent has been fully deployed the valve 48 can be closed in order to terminate suction and thus the reversal of blood flow in the carotid artery. As the procedure is now completed, and referring to FIG. 7, the first balloon 30 can then be deflated in order to allow normal blood flow to resume. It will be appreciated that while the above description refers to the implanting of a stent the present invention is not limited to such a procedure and may be utilised in multiple alternative vascular procedures where embolization may occur. It will also be understood that procedures involving the implanting of a stent may involve numerous steps to fully deploy the stent, including the use of balloons or other surgical devices in order to deploy and shape the stent, and during any such procedures where there is a risk of the formation of emboli the surgeon can open the valve 48 in order to establish reverse blood flow into the syringe 38 in order to capture any such emboli which may be generated during the procedure. The syringe 38 may be emptied and re-primed at any stage during the surgical procedure in order to generate the desired suction. In addition this re-priming could effectively be achieved by removing the syringe 38 and replacing it with an emptied and possibly pre-primed syringe. Additionally or alternatively a two way valve (not shown) could be provided which would allow the syringe 38 to be emptied while remaining connected to the remainder of the system 10.

Figure 9:
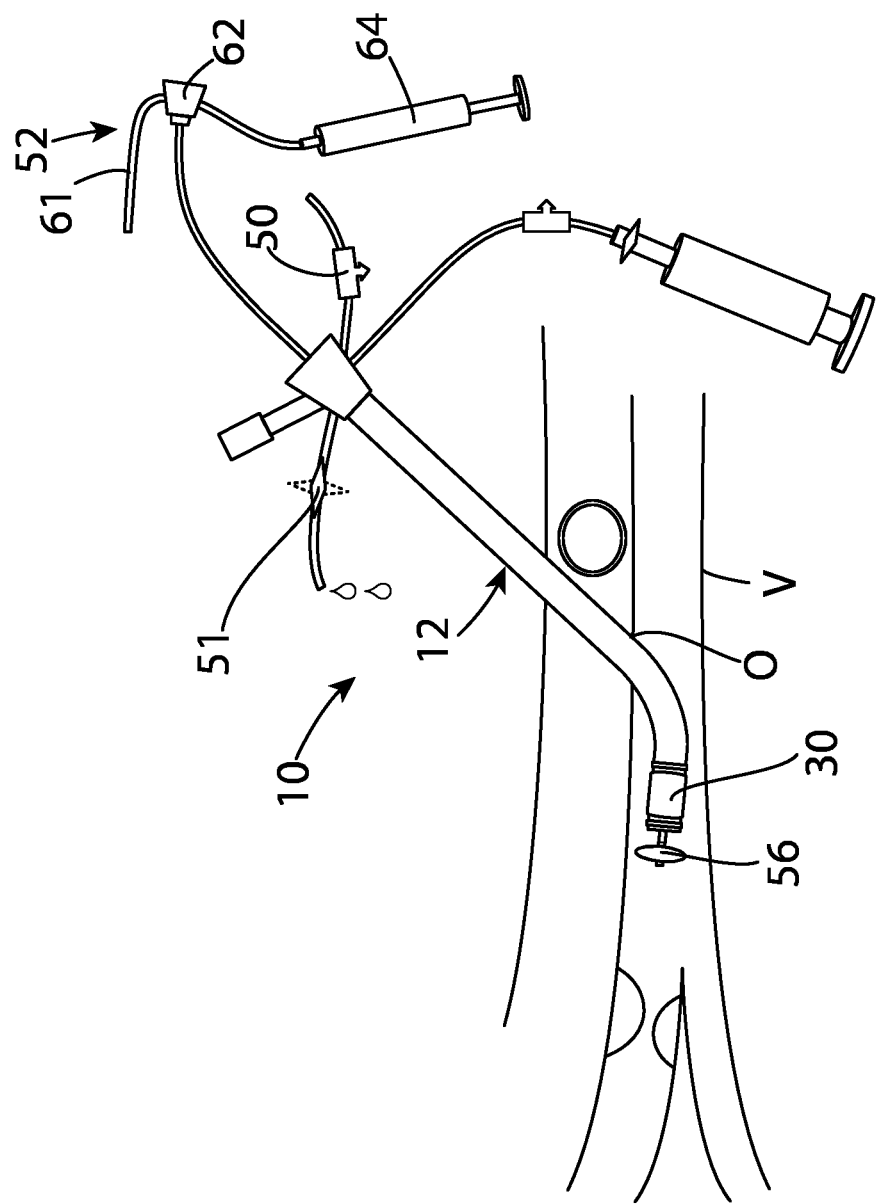
FIG. 9 illustrates the inflation of a second balloon forming part of the vascular closure device.

Turning then to FIG. 8, as the vascular surgical procedure is now complete it is necessary to withdraw the sheath 12 from the blood vessel V and to effect closure of the opening O in the blood vessel V. The catheter 54 of the vascular closure device 52 is thus passed through the haemostatic valve 46 and down the main lumen 18 of the sheath 12 while the distal end 16 remains within the blood vessel V, such that the second balloon 56 on the distal end of the catheter 54 enters the blood vessel V beyond the distal end 16 of the sheath 12. The second balloon 56 is then inflated or otherwise displaced into an expanded state as shown in FIG. 9, preferably by the introduction of a fluid such as a saline solution or other suitable fluid via one of the lumens in the catheter 54.

Figure 10:
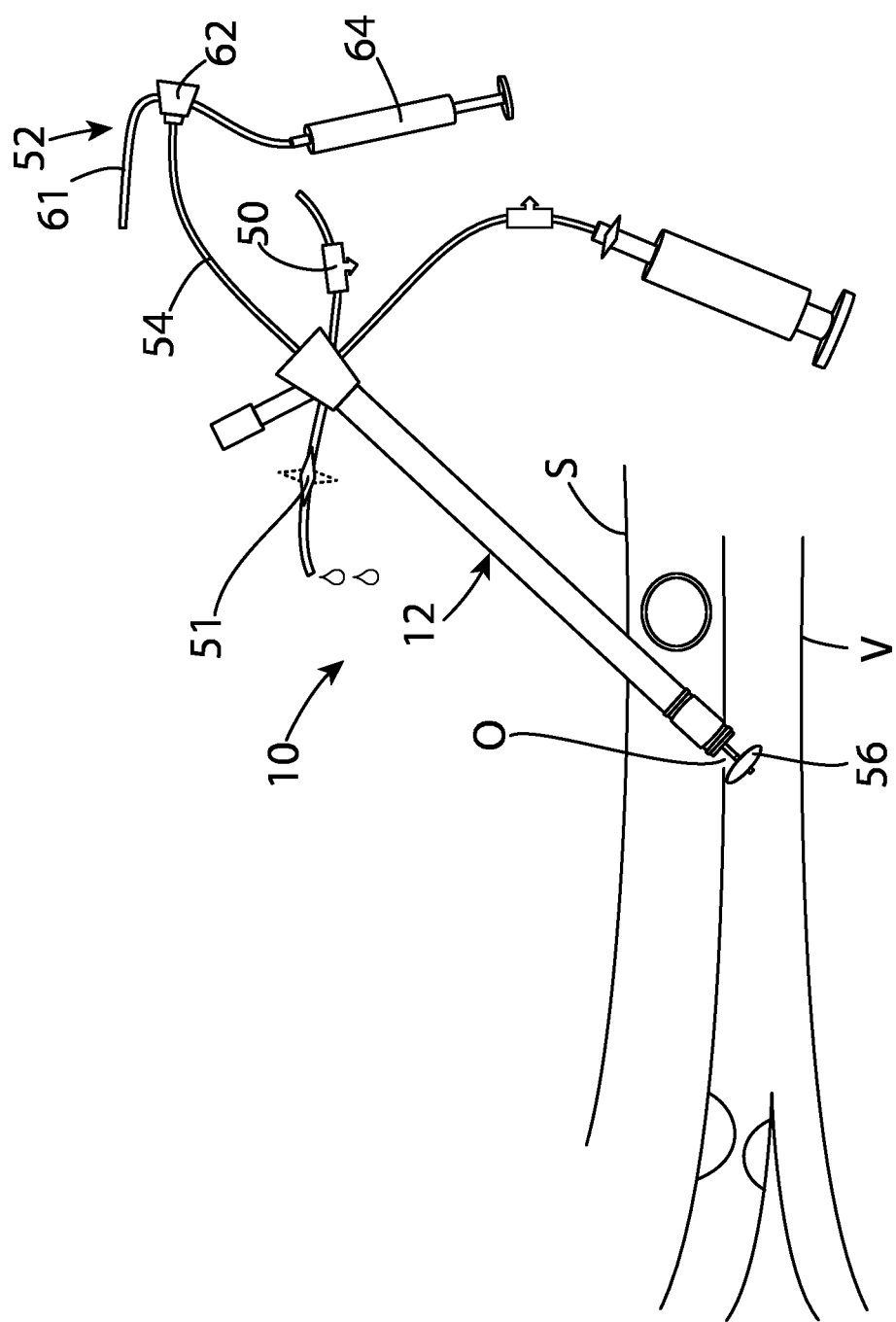
FIG. 10 illustrates withdrawal of the sheath from the carotid artery with the inflated second balloon remaining within the artery.
Figure 11:
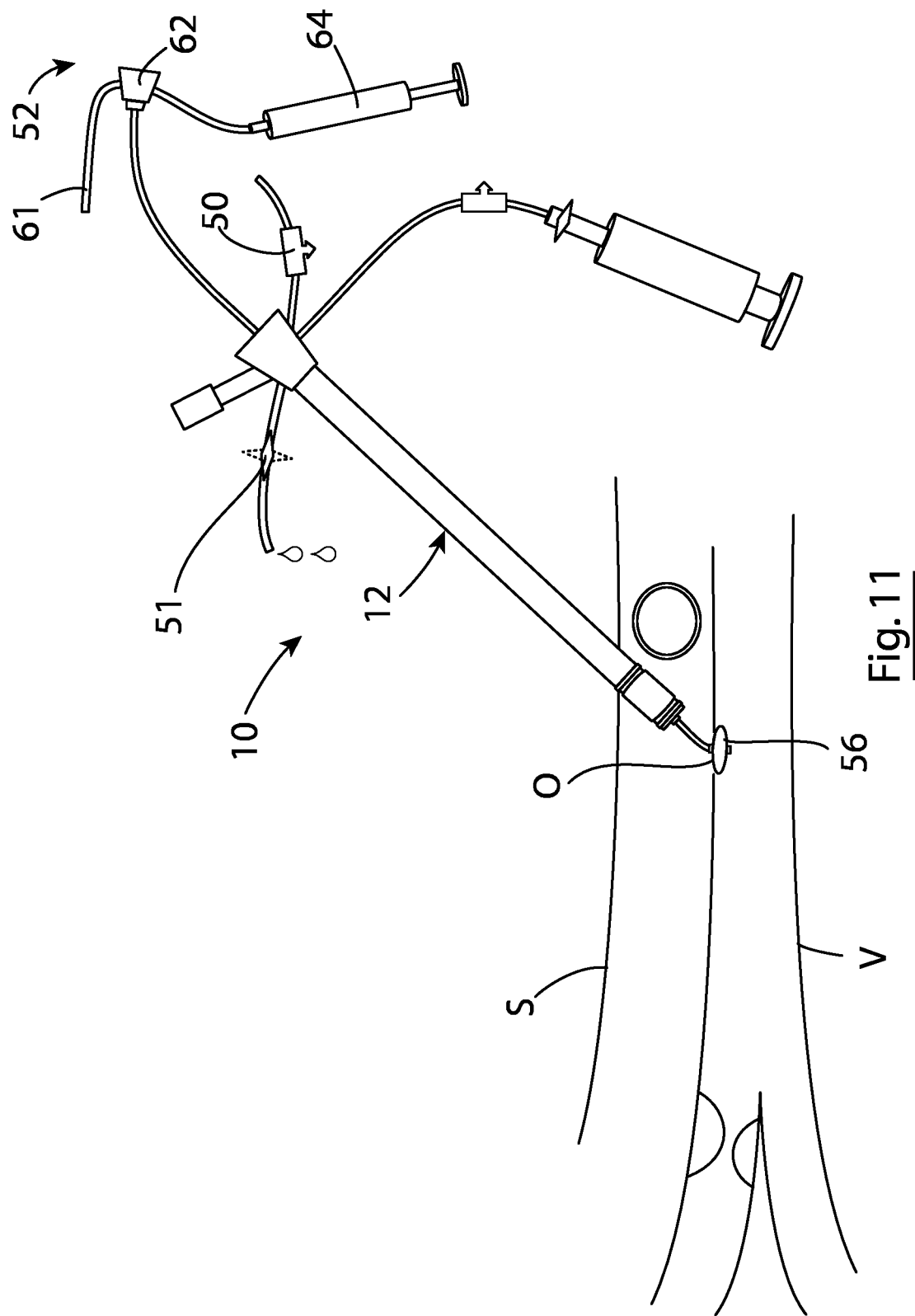
FIG. 11 illustrates the further withdrawal of the sheath and occlusion of an arteriotomy or opening in the carotid artery by the second balloon.

At this point, and referring to FIG. 10, the distal end 16 of the sheath 12 is withdrawn through the opening O in the blood vessel V, so that it sits just above the vessel V, and below but not withdrawn from the skin surface S, the proximal and distal markers 32, 34 allowing this accurate positioning to be achieved by the surgeon. Additionally or alternatively, the visible markers 70 on the exterior of the shaft of the catheter 54 may be used to indicate the precise location of the distal end 16 in relation to the second balloon 56. This retraction of the sheath 12 will also draw the inflated second balloon 56, which is preferably ellipsoid in shape, towards the opening O in the blood vessel V. Referring to FIG. 11, the sheath 12 and/or catheter 54 are further withdrawn until the second balloon 56 is drawn against the opening O in order to occlude same. The proximal marker 58 allows the surgeon to determine when the surface of the second balloon 56 is positioned against the opening O in the blood vessel V. Additionally or alternatively the valve 51 connected to the haemostatic valve 46 is operable to allow dripping of pulsatile blood flow and therefore allow the surgeon or other operator to determine that they are in the lumen of the vessel V.

Figure 12:
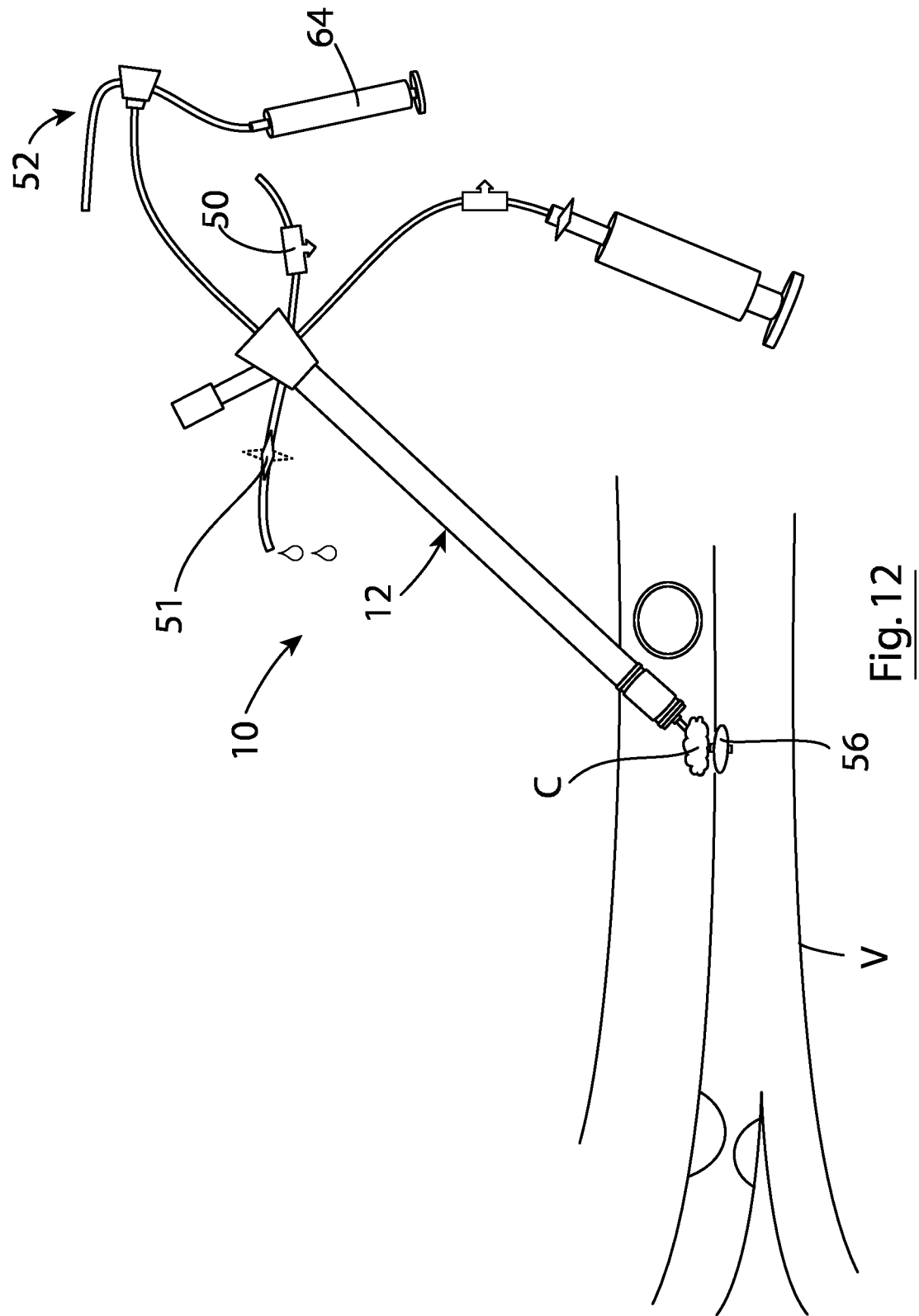
FIG. 12 illustrates the application of extravascular sealant to the opening in the carotid artery.
Figure 18:
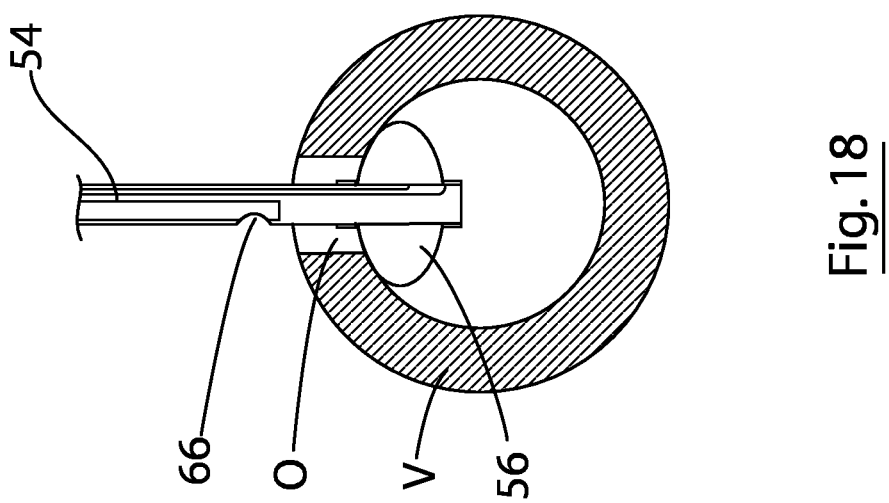
FIG. 18 illustrates a cross sectional view of a blood vessel with the vascular closure device of the surgical system located therein.

At this point the distal end 16 of the sheath 12 remains below the skin surface S and is positioned above the vessel arteriotomy but out of the blood vessel V. Referring to FIG. 12, with the second balloon 56 occluding the opening O the sealant delivery system 64 is operated by the surgeon in order to dispense sealant C from an outlet 66 adjacent the distal end of the catheter 54 and thus about the opening O onto the exterior of the blood vessel V to surround and occlude the opening O. A more detailed view of the positioning of the catheter 54 and balloon 56 within the blood vessel V is shown in FIG. 18.

Figure 13:
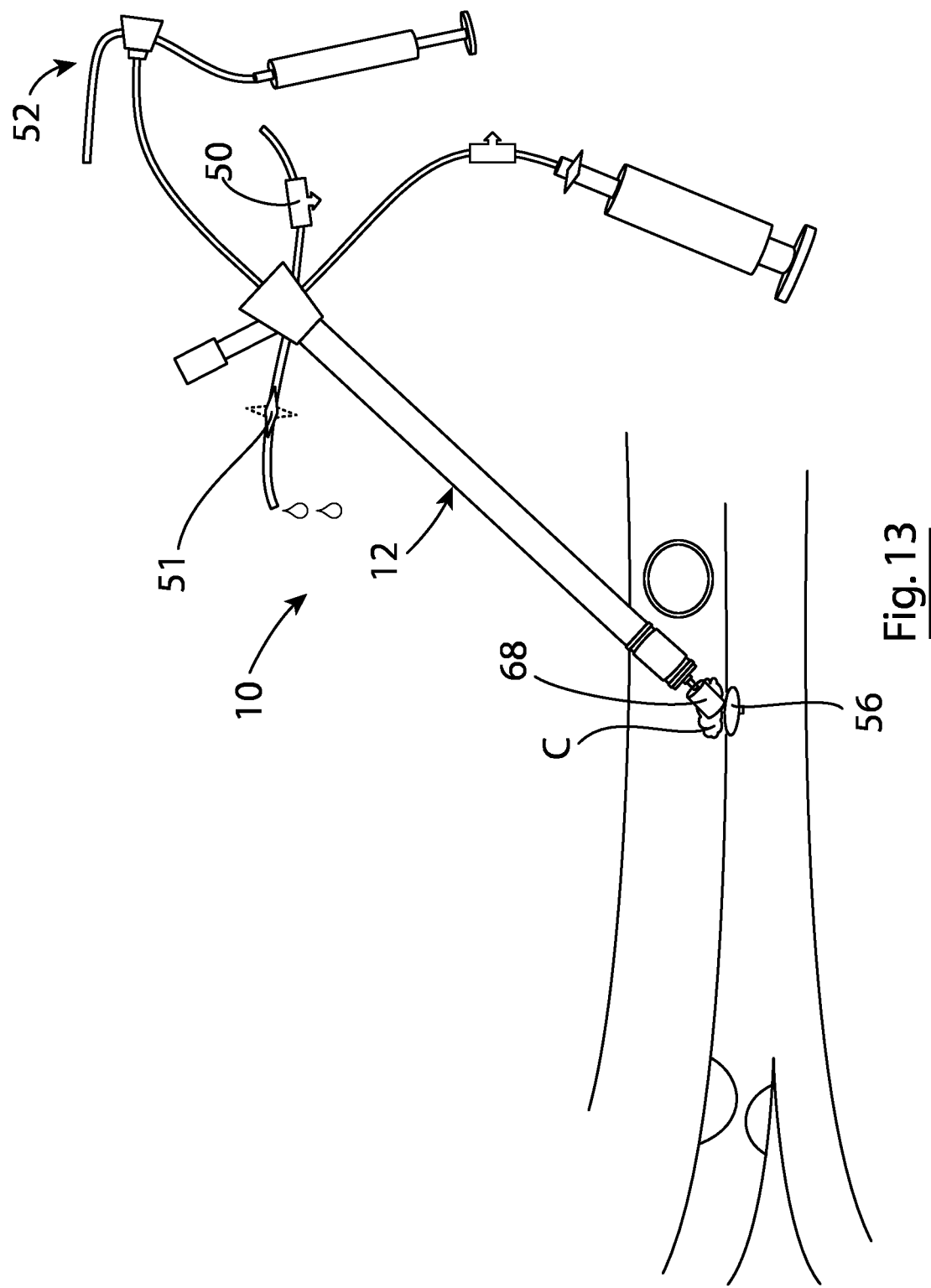
FIG. 13 illustrates the application of a vascular plug to the extra vascular sealant via the sheath with the second balloon inflated.
Figure 14:
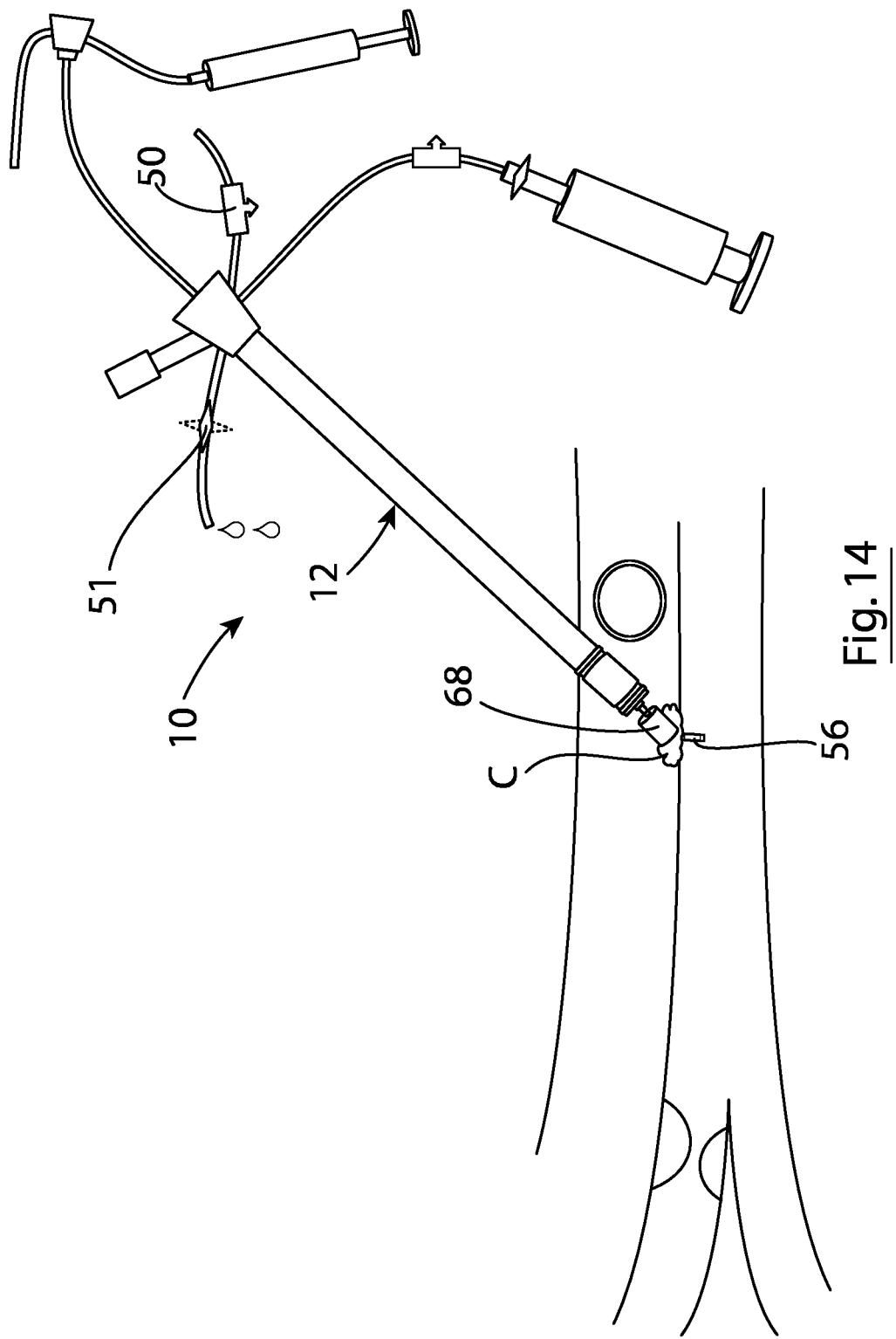
FIG. 14 illustrates deflation of the second balloon for withdrawal from the blood vessel via the sheath.
Figure 15:
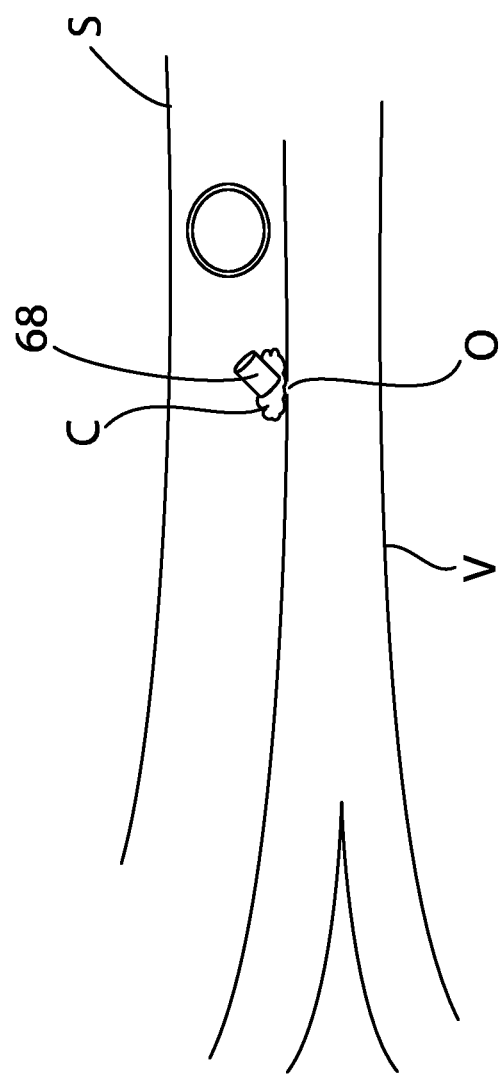
FIG. 15 illustrates the complete withdrawal of the percutaneous vascular surgical system with the sealant and plug remaining in place about the opening in the blood vessel.
Figure 16:
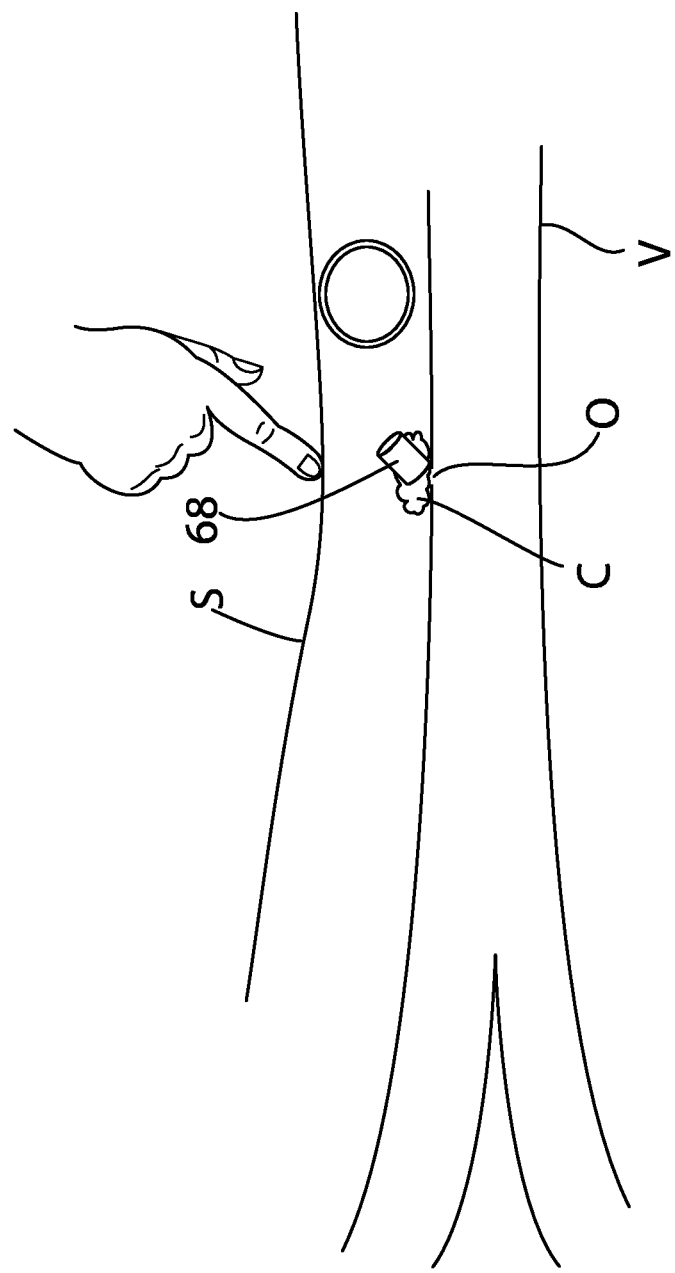
FIG. 16 illustrates the application of manual compression to the closure site.

Referring to FIG. 13, the vascular plug 68 is then advanced over the catheter 54 and down the main lumen 18 of the sheath 12 to be deposited in the extravascular sealant C and thus additionally occluding the opening O in the blood vessel V. Once a suitable time has elapsed to allow the sealant to be fully activated, and once the plug 68 has deployed and expanded, as illustrated in FIG. 14, the second balloon 56 is deflated or otherwise displaced into the collapsed state as illustrated, and is then withdrawn through the opening O and the vascular plug 68, allowing the catheter 54 and sheath 12 to then be fully withdrawn from the patient, as shown in FIG. 15, leaving only the vascular plug 68 and extravascular sealant C about the opening O.

The surgeon will then apply manual compression through the skin surface S to the vascular plug 68 for a short period of time, for example two to three minutes, in order to allow the vascular sealant C to set and thus fully seal the opening O. At this point the surgical procedure is complete and with significantly lower risk of wound complications and in the case of carotid artery stenosis, lower risk of cranial nerve damage. In addition the surgical system 10 of the invention allows procedures to be performed without the need for a general anaesthetic, and as surgery is not required it can be performed as an outpatient procedure under local anaesthetic.

Referring now to FIG. 20 there is illustrated an alternative embodiment of a vascular closure device forming part of the system 10 of the invention, and generally indicated as 152. In this alternative embodiment like components have been accorded like reference numerals and unless otherwise stated perform a like function. The closure device 152 may be used as a direct alternative to the closure device 52 to form a component part of the overall vascular surgical system 10 of the invention. The closure device 152 comprises a catheter 154 on which is provided, at or adjacent a distal end, a closure member in the form of a second balloon 156 and a third balloon 157 spaced from the first balloon 156 in a direction away from the distal end of the catheter 154. The catheter 154 comprises first and second inflation lumens 172 and 174, shown in the section view AA forming part of FIG. 20, to respectively inflate/deflate the second and third balloons 156, 157, allowing for independent inflation and/or deflation thereof, although it is also envisaged that a single lumen could be employed to effect the simultaneous inflation/deflation of the balloons 156, 157. It will be understood that the balloons 156, 157 could be of any other suitable form, for example a reversibly expandable/collapsible disc or the like, formed from a flexible or foldable material, for example Nitinol® or the like. The catheter 154 preferably additionally comprises a sealant delivery lumen 176 to facilitate delivery of an optional sealant or the like to the closure site via an outlet 166.

In use the closure device 152 is delivered through the sheath 12 as hereinbefore described with reference to the closure device 52, with both balloons 156, 157 delated or collapsed. The second balloon 156 is inflated once located internally of the blood or other vessel V, adjacent the puncture site O, before the third balloon 157 is inflated, therefore capturing or sandwiching the walls of the vessel V defining the puncture site O between the two balloons 156, 157 as illustrated. The location of the balloons 156, 157 prior to inflation may be determined by the provision of one or more radiopaque markers (not shown) or the like, preferably provided on the catheter 154, and preferably one marker on either side of at least the second balloon 156. If being used, a sealant may then be dispensed through the sealant lumen 176 to issue from the outlet 166. If no sealant is employed a suitable period of time is simply allowed to elapse that is sufficient to allow the puncture to reduce in size, before the balloons 156, 157 are deflated or collapsed and withdrawn from the vessel V as hereinbefore described, preferably followed by a brief manual compression.

Referring to FIGS. 21 to 23 there is illustrated a still further alternative embodiment of a vascular closure device forming part of the system 10 of the invention, and generally indicated as 252. In this alternative embodiment like components have been accorded like reference numerals and unless otherwise stated perform a like function. The closure device 252 may be used as a direct alternative to the closure device 52 or 152 to form a component part of the overall vascular surgical system 10 of the invention. The closure device 252 comprises a catheter 254 on which is provided, at or adjacent a distal end of the catheter 254, a closure member in the form of a reversible expandable umbrella shaped element 256 which may be formed from any suitable material, for example a covered mesh or the like. The umbrella element 256 is displaceable between a collapsed state as illustrated in FIG. 21, in which the umbrella element 256 may be delivered to the puncture site through the main lumen of the sheath 12. As illustrated in FIG. 22, once located within the artery the umbrella element 256 is advanced out of the sheath 12 and is displaced into an expanded state as shown before being drawn back against the interior wall of the artery, surrounding the puncture site and allowing the puncture to reduce in size over a short period of time. At this point, and referring to FIG. 23, the umbrella element 256 is displaced into a collapsed state, which may be the same as that shown in FIG. 21 or may be a fully reversed or inverted collapsed state to reduce resistance to withdrawal, before being withdrawn from the artery as hereinbefore described. A sealant may optionally be dispensed extra-arterially through the multi-lumen catheter 254 or through the sheath 12 to seal the arteriotomy. Alternatively the closure device 252 may be used without a sealant to effect the temporary blockage of the puncture until the arteriotomy is small enough to be closed by brief external manual compression.

It will thus be appreciated that the percutaneous vascular surgical system 10 and method of the present invention allows percutaneous access to the vascular system in order to perform vascular surgery, and a significant advantage is that all of the steps to access and egress the artery are performed using a single device and can be operated simply and efficiently by a single surgeon. The system 10 is also compatible with any medical device that can be deployed via the main lumen 18, making it suitable for use in numerous procedures.

It will also be appreciated that while the vascular closure device 52, 152, 252 is disclosed as part of the surgical system 10 of the present invention, it could be used in isolation from the remainder of the surgical system 10, and conversely the surgical system 10 could utilise an alternative vascular closure system (not shown) for example one or more commercially available closure systems.

The invention claimed is:

1. A percutaneous vascular surgical system comprising:
   a sheath having a proximal end and a distal end and defining a main lumen extending between the proximal and distal ends;
   at least one auxiliary lumen defined by the sheath;
   a reversibly inflatable first balloon located about the sheath adjacent the distal end and in fluid communication with the at least one auxiliary lumen, the first balloon being dimensioned when inflated to fully occlude a blood vessel through which vascular access of the sheath is achieved while leaving the distal end open;
   a negative pressure generator selectively connectable to the main lumen operable to reverse blood flow in the blood vessel; and
   a vascular closure device operable through the main lumen to seal an opening in a wall of the blood vessel.

2. The surgical system of claim 1 in which the at least one auxiliary lumen is disposed concentrically of the main lumen.

3. The surgical system of claim 1 in which a sidewall of the sheath is reinforced.

4. The surgical system of claim 1 in which the sheath is capable of being preformed.

5. The surgical system of claim 1 in which the sheath is angulated adjacent the distal end.

6. The surgical system of claim 1 in which the sheath comprises a circumferentially extending annular channel on an exterior of a sidewall of the sheath into which the first balloon, when deflated, is at least partially recessed.

7. The surgical system of claim 1 in which the negative pressure generator comprises an at least partially evacuatable reservoir.

8. The surgical system of claim 1 in which the negative pressure generator is configured to generate a negative pressure of 50 mm Hg or less.

9. The surgical system of claim 1 in which the negative pressure generator comprises a manually operable syringe.

10. The surgical system of claim 1 comprising a manually operable valve disposed between the negative pressure generator and the main lumen.

11. The surgical system of claim 1 comprising a port adapted for connection to a blood pressure gauge.

12. The surgical system of claim 1 in which the sheath comprises a marker on either side of the first balloon.

13. The surgical system of claim 1 in which the vascular closure device comprises a closure member displaceable between a collapsed and expanded state, and a catheter on which the closure member is mounted to allow the closure member to be delivered through the main lumen.

14. The surgical system of claim 13 in which the closure member comprises a second balloon.

15. The surgical system of claim 13 in which the vascular closure device comprises a sealant delivery system operable through the sheath to dispense a sealant about an opening in a wall of a blood vessel through which vascular access of the sheath was achieved.

16. The surgical system of claim 15 in which the catheter comprises an internal bore through which the sealant may be delivered.

17. The surgical system of claim 13 comprising a plug deliverable through the main lumen.

18. The surgical system of claim 17 in which the plug is deliverable over and along the catheter.

19. A method of vascular surgery comprising the steps of percutaneous insertion of a multi lumen sheath into a blood vessel; inflating a first balloon located about a distal end of the sheath in order to occlude the blood vessel, the first balloon being dimensioned when inflated to fully occlude the blood vessel while leaving the distal end open; performing a surgical procedure within the blood vessel via the sheath; generating suction through the sheath during the surgical procedure in order to reverse blood flow in the blood vessel; deflating the first balloon; prior to removing the sheath from the blood vessel, passing a vascular closure device through the sheath; withdrawing the sheath from the blood vessel and sealing an opening in the blood vessel through which the sheath was inserted with the vascular closure device.

20. A method according to claim 19 comprising passing a closure member of the vascular closure device through the sheath into the blood vessel; expanding the closure member from a collapsed state; withdrawing the sheath from the blood vessel with the closure member remaining in the blood vessel; and drawing the closure member against the opening.

21. A method according to claim 20 comprising the step of extravascular application of a sealant about the opening via the sheath.

22. A method according to claim 21 comprising the step of delivering a plug through the sheath and depositing the plug in or adjacent the sealant.

23. A method according to claim 20 comprising the step of collapsing the closure member and withdrawing the closure member from the blood vessel via the opening.

24. A method according to claim 19 comprising the step of applying manual compression against the opening.

25. A method according to claim 19 comprising utilising a negative pressure of 50 mmHg or less in order to generate the suction, and effect a reversal of flow.

26. A method according to claim 19 comprising the step of effecting the reversal of blood flow in the vessel and surrounding vessels through the application of the negative pressure in order to assist in organ perfusion and/or emboli removal during a vascular intervention.

\* \* \* \* \*